(12) United States Patent
Earl et al.

(10) Patent No.: US 11,992,392 B2
(45) Date of Patent: May 28, 2024

(54) NEGATIVE PRESSURE WOUND TREATMENT APPARATUSES AND METHODS WITH INTEGRATED ELECTRONICS

(71) Applicant: Smith & Nephew PLC, Watford (GB)

(72) Inventors: Michael Earl, York (GB); Frederick Jethro Harrison, Cambridge (GB); William Kelbie, Inverness (GB); Reece Knight, Kingston upon Hull (GB); David Peter Lloyd, North Ferriby (GB); Joseph William Robinson, Papworth Everard (GB); Daniel Lee Steward, Hull (GB); Grant West, Luton (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 17/985,051

(22) Filed: Nov. 10, 2022

(65) Prior Publication Data

US 2023/0142359 A1    May 11, 2023

Related U.S. Application Data

(63) Continuation of application No. 16/760,162, filed as application No. PCT/EP2018/079345 on Oct. 25, 2018, now Pat. No. 11,497,653.

(30) Foreign Application Priority Data

Nov. 1, 2017  (GB) .................................... 1718070
Apr. 5, 2018  (GB) .................................... 1805582

(51) Int. Cl.
*A61F 13/00* (2006.01)
*A61F 13/05* (2024.01)
(Continued)

(52) U.S. Cl.
CPC ........ *A61F 13/05* (2024.01); *A61F 13/00059* (2013.01); *A61M 1/732* (2021.05);
(Continued)

(58) Field of Classification Search
CPC ........ A61F 13/00068; A61F 13/00059; A61M 1/732; A61M 1/90; A61M 1/915;
(Continued)

(56) References Cited

U.S. PATENT DOCUMENTS 3,874,387 A    4/1975  Barbieri
4,224,941 A    9/1980  Stivala
(Continued)

FOREIGN PATENT DOCUMENTS

CN    201664463 U    12/2010
DE    19844355 A1    4/2000
(Continued)

OTHER PUBLICATIONS

"Seal," Definition of Seal by Merriam-Webster, Retrieved from the internet: https://www.merriam-webster.com/dictionary/seal, Accessed on Aug. 11, 2021, 13 pages.
(Continued)

*Primary Examiner* — Nicholas J. Weiss
*Assistant Examiner* — Eric Rassavong
(74) *Attorney, Agent, or Firm* — Knobbe, Martens, Olson & Bear, LLP

(57) ABSTRACT

Disclosed herein are embodiments of a wound treatment apparatus with electronic components integrated within a wound dressing. In some embodiments, a wound dressing apparatus can comprise a wound contact layer, an absorbent layer over the wound contact layer, the absorbent layer comprising one or more apertures, a cover layer configured to cover and form a seal over the wound contact layer and the absorbent layer, and an electronics assembly comprising
(Continued)

a negative pressure source. A portion of the cover layer overlying the one or more apertures in the absorbent layer can be configured to be compressed within the aperture in the absorbent layer when negative pressure is applied to the wound dressing apparatus. The compressed cover layer can indicate a level of negative pressure below the cover layer. In some embodiments, the wound dressing apparatus can comprise an indicator material layer and a cover layer configured to cover and form a seal over the wound contact layer and the indicator material layer. The indicator material layer can be configured to protrude relative to a surrounding surface of an upper surface of the wound dressing apparatus when negative pressure is applied to the wound dressing apparatus and the protruding indicator material layer indicates a level of negative pressure below the cover layer.

19 Claims, 42 Drawing Sheets

(51) Int. Cl.
*A61M 1/00* (2006.01)
*A61M 39/24* (2006.01)

(52) U.S. Cl.
CPC .............. *A61M 1/90* (2021.05); *A61M 1/915* (2021.05); *A61M 1/962* (2021.05); *A61M 1/964* (2021.05); *A61M 1/966* (2021.05); *A61M 39/24* (2013.01); *A61M 2205/3306* (2013.01); *A61M 2205/3344* (2013.01); *A61M 2205/3368* (2013.01); *A61M 2205/50* (2013.01); *A61M 2205/582* (2013.01); *A61M 2205/583* (2013.01); *A61M 2205/587* (2013.01); *A61M 2205/7518* (2013.01); *A61M 2205/8206* (2013.01)

(58) Field of Classification Search
CPC ...... A61M 1/962; A61M 1/964; A61M 39/24; A61M 2205/3306; A61M 2205/3344; A61M 2205/3368; A61M 2205/50; A61M 2205/582; A61M 2205/583; A61M 2205/587; A61M 2205/7518; A61M 2205/8206
See application file for complete search history.

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 5,989,245 A | 11/1999 | Prescott |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,927,344 B1 | 8/2005 | Gall et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| 7,779,625 B2 | 8/2010 | Joshi et al. |
| D625,422 S | 10/2010 | Arbesman et al. |
| 7,815,616 B2 | 10/2010 | Boehringer et al. |
| 7,837,673 B2 | 11/2010 | Vogel |
| 7,846,141 B2 | 12/2010 | Weston |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,080,702 B2 | 12/2011 | Blott et al. |
| 8,092,441 B2 | 1/2012 | Sugito |
| 8,158,844 B2 | 4/2012 | McNeil |
| 8,167,869 B2 | 5/2012 | Wudyka |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,460,255 B2 | 6/2013 | Joshi et al. |
| 8,500,776 B2 | 8/2013 | Ebner |
| 8,529,548 B2 | 9/2013 | Blott et al. |
| 8,545,466 B2 | 10/2013 | Andresen et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,641,691 B2 | 2/2014 | Fink et al. |
| 8,641,693 B2 | 2/2014 | Locke et al. |

(56) References Cited

U.S. PATENT DOCUMENTS

| | | |
|---|---|---|
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,870,837 B2 | 10/2014 | Locke et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,265,665 B2 | 2/2016 | Robinson et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,560,975 B2 | 2/2017 | Mei et al. |
| D787,690 S | 5/2017 | Mackay et al. |
| 9,737,649 B2 | 8/2017 | Begin et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,016,544 B2 | 7/2018 | Coulthard et al. |
| 10,046,095 B1 | 8/2018 | Middaugh et al. |
| 10,086,117 B2 | 10/2018 | Locke et al. |
| 2003/0212357 A1 | 11/2003 | Pace |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude |
| 2008/0051716 A1 | 2/2008 | Stutz |
| 2009/0012484 A1 | 1/2009 | Nielsen et al. |
| 2009/0048556 A1* | 2/2009 | Durand ............... A61K 9/0009 604/20 |
| 2010/0022990 A1 | 1/2010 | Karpowicz et al. |
| 2010/0100160 A1 | 4/2010 | Edman et al. |
| 2010/0137775 A1* | 6/2010 | Hu ..................... A61F 13/0256 602/54 |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2010/0305490 A1* | 12/2010 | Coulthard ........... A61F 13/0206 604/313 |
| 2011/0092927 A1 | 4/2011 | Wilkes et al. |
| 2011/0112492 A1* | 5/2011 | Bharti ................. A61M 1/78 604/319 |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0215638 A1 | 8/2013 | Dabov et al. |
| 2014/0100536 A1 | 4/2014 | Angel |
| 2014/0298928 A1 | 10/2014 | Duesterhoft et al. |
| 2014/0343518 A1 | 11/2014 | Riesinger |
| 2015/0057625 A1* | 2/2015 | Coulthard ........... A61F 13/0216 604/319 |
| 2015/0174304 A1* | 6/2015 | Askem ............... A61F 13/00042 604/319 |
| 2015/0202354 A1* | 7/2015 | Wall ..................... A61L 15/42 604/319 |
| 2016/0015873 A1 | 1/2016 | Robinson et al. |
| 2016/0166438 A1* | 6/2016 | Rovaniemi ............ A61F 13/42 493/320 |
| 2016/0199546 A1 | 7/2016 | Chao |
| 2016/0242964 A1* | 8/2016 | Rapp .................... A61F 13/025 |
| 2016/0270700 A1* | 9/2016 | Baxi .................... A61B 5/6828 |
| 2016/0271305 A1 | 9/2016 | Kurihara et al. |
| 2016/0361473 A1 | 12/2016 | Robinson et al. |
| 2017/0112974 A1* | 4/2017 | Fujisaki ................ A61M 1/962 |
| 2017/0112975 A1 | 4/2017 | Fujisaki |
| 2017/0127525 A1 | 5/2017 | Schonholz |
| 2017/0202711 A1 | 7/2017 | Cernasov et al. |
| 2017/0232189 A1 | 8/2017 | Qin et al. |
| 2017/0296714 A1 | 10/2017 | Locke et al. |
| 2017/0319758 A1 | 11/2017 | Eddy et al. |
| 2017/0319761 A1 | 11/2017 | Locke et al. |
| 2017/0326277 A1 | 11/2017 | Huang |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1* | 4/2018 | Wu ........................ A61M 1/96 |
| 2018/0200414 A1 | 7/2018 | Askem et al. |
| 2018/0272052 A1* | 9/2018 | Locke .................. A61M 1/913 |
| 2018/0296397 A1* | 10/2018 | Askem .................. A61M 1/79 |
| 2018/0318137 A1 | 11/2018 | Donda et al. |
| 2018/0318165 A1* | 11/2018 | Donda .................. A61F 13/02 |
| 2018/0353771 A1 | 12/2018 | Kim et al. |
| 2019/0021911 A1 | 1/2019 | Askem et al. |
| 2019/0125943 A1* | 5/2019 | Askem .................. A61M 1/96 |
| 2019/0142644 A1* | 5/2019 | Askem ................ A61M 1/962 604/543 |
| 2019/0143007 A1* | 5/2019 | Askem .................. A61M 1/74 604/319 |
| 2019/0159938 A1* | 5/2019 | Askem .................. A61M 1/784 |
| 2019/0192350 A1 | 6/2019 | Gowans et al. |
| 2019/0282737 A1* | 9/2019 | Beadle ............... A61F 13/0216 |
| 2020/0022846 A1* | 1/2020 | Beadle ................ A61F 13/022 |
| 2020/0170843 A1 | 6/2020 | Collinson et al. |
| 2021/0001022 A1 | 1/2021 | Lin |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |

(56) References Cited

FOREIGN PATENT DOCUMENTS

| | | | |
|---|---|---|---|
| EP | 2603699 | A1 | 6/2013 |
| EP | 1893145 | B1 | 7/2013 |
| EP | 2370142 | B1 | 7/2013 |
| EP | 2279017 | B1 | 8/2013 |
| EP | 2370117 | B1 | 8/2013 |
| EP | 2258443 | B1 | 9/2013 |
| EP | 1848390 | B1 | 12/2013 |
| EP | 1875081 | B1 | 12/2013 |
| EP | 2271381 | B1 | 12/2013 |
| EP | 2160166 | B1 | 1/2014 |
| EP | 1565219 | B1 | 2/2014 |
| EP | 2305325 | B1 | 4/2014 |
| EP | 2323712 | B1 | 4/2014 |
| EP | 2451498 | B1 | 4/2014 |
| EP | 2051675 | B1 | 6/2014 |
| EP | 1485613 | B1 | 7/2014 |
| EP | 1545644 | B1 | 8/2014 |
| EP | 2349154 | B1 | 8/2014 |
| EP | 2146759 | B1 | 9/2014 |
| EP | 2416816 | B1 | 10/2014 |
| EP | 2468323 | B1 | 10/2014 |
| EP | 2658493 | B1 | 10/2014 |
| EP | 1850818 | B1 | 12/2014 |
| EP | 2268348 | B1 | 12/2014 |
| EP | 2561128 | B1 | 1/2015 |
| EP | 2829287 | A1 | 1/2015 |
| EP | 2683285 | B1 | 2/2015 |
| EP | 2470136 | B1 | 3/2015 |
| EP | 2503974 | B1 | 5/2015 |
| EP | 2249894 | B1 | 8/2015 |
| EP | 2802366 | B1 | 8/2015 |
| EP | 2438302 | B1 | 9/2015 |
| EP | 2346545 | B1 | 10/2015 |
| EP | 2438301 | B1 | 10/2015 |
| EP | 2802304 | B1 | 12/2015 |
| EP | 2852421 | B1 | 1/2016 |
| EP | 2410962 | B1 | 3/2016 |
| EP | 2640436 | B1 | 3/2016 |
| EP | 2855937 | B1 | 5/2016 |
| EP | 2433594 | B1 | 6/2016 |
| EP | 2919730 | B1 | 6/2016 |
| EP | 2861869 | B1 | 7/2016 |
| EP | 2945584 | B1 | 7/2016 |
| EP | 2293749 | B1 | 8/2016 |
| EP | 2305327 | B1 | 10/2016 |
| EP | 2467086 | B1 | 10/2016 |
| EP | 2470135 | B1 | 10/2016 |
| EP | 2767305 | B1 | 10/2016 |
| EP | 2282788 | B1 | 12/2016 |
| EP | 2462956 | B2 | 3/2017 |
| EP | 3139878 | A1 | 3/2017 |
| EP | 1587502 | B1 | 5/2017 |
| EP | 1587554 | B1 | 5/2017 |
| EP | 2731563 | B1 | 5/2017 |
| EP | 2968871 | B1 | 7/2017 |
| EP | 2632613 | B1 | 8/2017 |
| EP | 2888478 | B1 | 8/2017 |
| EP | 2937107 | B1 | 8/2017 |
| EP | 2967627 | B1 | 8/2017 |
| EP | 3062751 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 2675493 | B1 | 10/2017 |
| EP | 3068455 | B1 | 10/2017 |
| EP | 2558046 | B2 | 11/2017 |
| EP | 2736548 | B1 | 11/2017 |
| EP | 3052158 | B1 | 11/2017 |
| EP | 2593058 | B1 | 3/2018 |
| EP | 3139880 | B1 | 3/2018 |
| EP | 1496822 | B1 | 8/2018 |
| EP | 2879633 | B1 | 8/2018 |
| EP | 2227203 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 3062753 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3143974 | B1 | 4/2019 |
| EP | 2285432 | B2 | 6/2019 |
| EP | 3050545 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 2244756 | B1 | 12/2019 |
| EP | 2968702 | B1 | 12/2019 |
| FR | 2939320 | A1 | 6/2010 |
| GB | 2511523 | A | 9/2014 |
| JP | H04354722 | A | 12/1992 |
| RU | 131622 | U1 | 8/2013 |
| WO | WO-2009098696 | A2 | 8/2009 |
| WO | WO-2009120951 | A2 | 10/2009 |
| WO | WO-2011144888 | A1 | 11/2011 |
| WO | WO-2013007973 | A2 | 1/2013 |
| WO | WO-2014020440 | A1 * | 2/2014 ....... A61F 13/00012 |
| WO | WO-2014099709 | A1 | 6/2014 |
| WO | WO-2014116816 | A1 | 7/2014 |
| WO | WO-2016126560 | A1 | 8/2016 |
| WO | WO-2017079174 | A1 | 5/2017 |
| WO | WO-2017196888 | A1 | 11/2017 |
| WO | WO-2018056060 | A1 | 3/2018 |
| WO | WO-2018115461 | A1 | 6/2018 |
| WO | WO-2018156730 | A1 | 8/2018 |
| WO | WO-2018158250 | A1 | 9/2018 |
| WO | WO-2018162613 | A1 | 9/2018 |
| WO | WO-2018164803 | A1 | 9/2018 |
| WO | WO-2018185138 | A1 | 10/2018 |
| WO | WO-2018192978 | A1 | 10/2018 |
| WO | WO-2018206420 | A1 | 11/2018 |
| WO | WO-2019053101 | A1 | 3/2019 |
| WO | WO-2019053106 | A1 | 3/2019 |
| WO | WO-2019086332 | A1 * | 5/2019 ....... A61F 13/00059 |
| WO | WO-2019086341 | A1 | 5/2019 |
| WO | WO-2019086475 | A1 | 5/2019 |
| WO | WO-2019193141 | A1 | 10/2019 |

OTHER PUBLICATIONS

International Preliminary Report on Patentability for Application No. PCT/EP2018/074701, dated Mar. 26, 2020, 8 pages.
International Preliminary Report on Patentability for Application No. PCT/EP2018/079345, dated May 14, 2020, 9 pages.
International Search Report and Written Opinion for Application No. PCT/EP2018/079345, dated Feb. 13, 2019, 14 pages.
International Search Report and Written Opinion for Application No. PCT/EP2018/074701, dated Jan. 4, 2019, 10 pages.
Merriam-Webster., "Integral," Retrieved from Internet URL: https://www.merriam-webster.com/dictionary/integral , on Dec. 13, 2021, 9 pages.

* cited by examiner

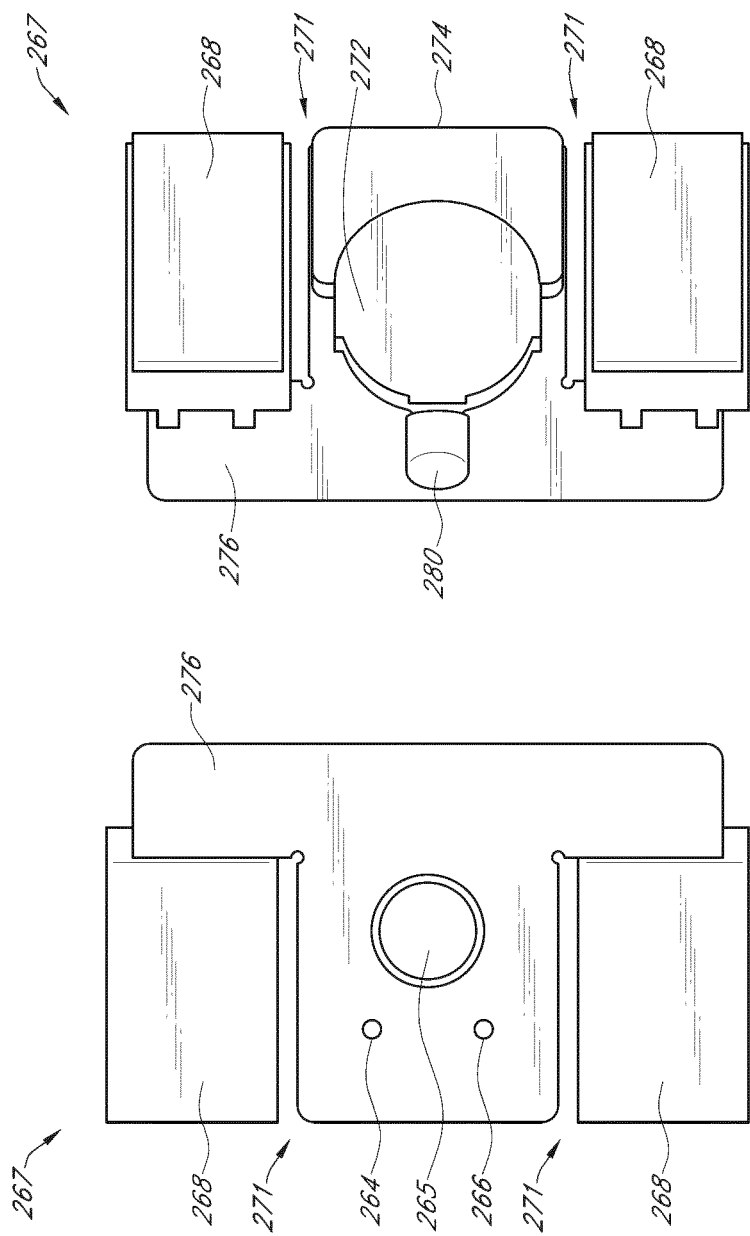

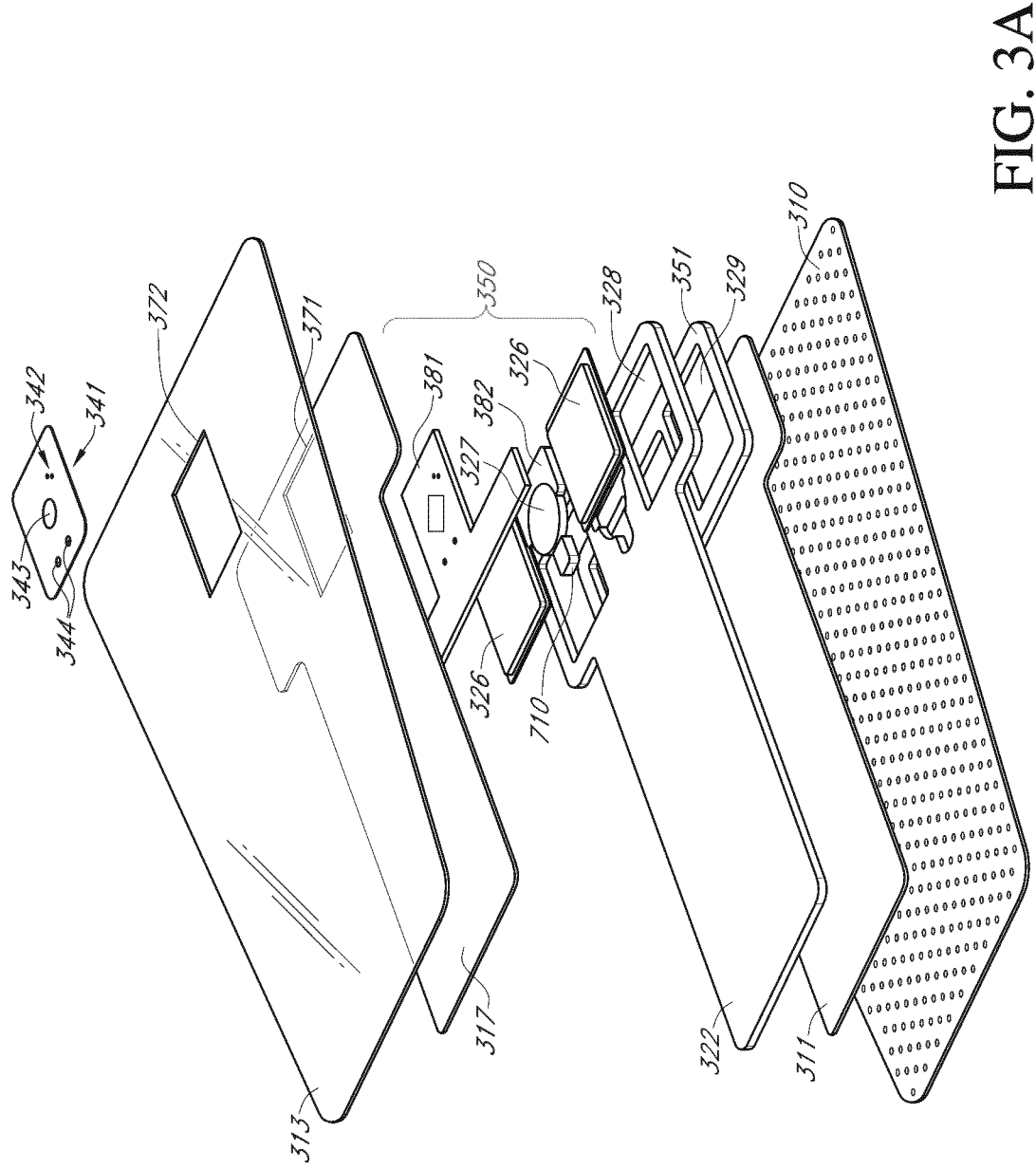

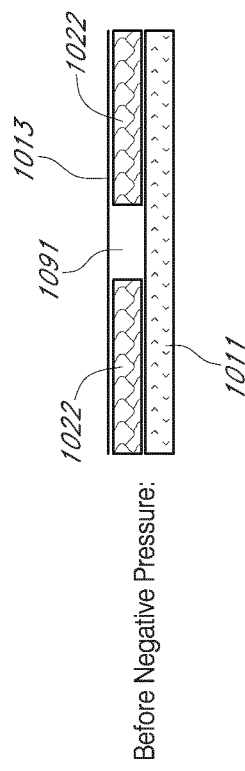
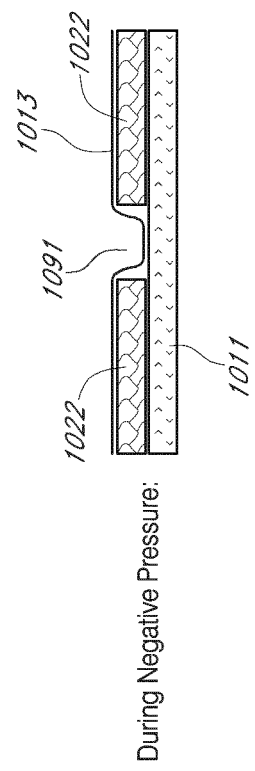

NEGATIVE PRESSURE WOUND TREATMENT APPARATUSES AND METHODS WITH INTEGRATED ELECTRONICS

RELATED APPLICATIONS

This application is a continuation of U.S. application Ser. No. 16/760,162, filed Apr. 29, 2020, which is a U.S. national stage application of International Patent Application No. PCT/EP2018/079345, filed Oct. 25, 2018, which claims priority to Great Britain Patent Application No. 1718070.4, filed on Nov. 1, 2017 and Great Britain Patent Application No. 1805582.2, filed on Apr. 5, 2018 which are hereby incorporated by reference in their entireties and made part of this disclosure.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Prior art dressings for use in negative pressure such as those described above have included a negative pressure source located in a remote location from the wound dressing. Negative pressure sources located remote from the wound dressing have to be held by or attached to the user or other pump support mechanism. Additionally, a tubing or connector is required to connect the remote negative pressure source to the wound dressing. The remote pump and tubing can be cumbersome and difficult to hide in or attach to patient clothing. Depending on the location of the wound dressing, it can be difficult to comfortably and conveniently position the remote pump and tubing. When used, wound exudate may soak into the dressing, and the moisture from the wound has made it difficult to incorporate electronic components into the dressing.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that applies the wound dressing and the negative pressure source simultaneously to a patient's wound. The negative pressure source and/or electronic components may be positioned between a wound contact layer and a cover layer of the wound dressing. An electronics assembly can be incorporated into a protective enclosure formed at least in part by a flexible film and the flexible film can have windows of porous material. These and other embodiments as described herein are directed to overcoming particular challenges involved with incorporating a negative pressure source and/or electronic components into a wound dressing.

According to one embodiment, a wound dressing apparatus can comprise a wound contact layer comprising a proximal wound-facing face and a distal face, wherein the proximal wound-facing face is configured to be positioned in contact with a wound, an absorbent layer over the wound contact layer, the absorbent layer comprising one or more apertures, a cover layer configured to cover and form a seal over the wound contact layer and the absorbent layer, and an electronics assembly comprising a negative pressure source, wherein a portion of the cover layer overlying the one or more apertures in the absorbent layer is configured to be compressed within the aperture in the absorbent layer when negative pressure is applied to the wound dressing apparatus and wherein the compressed cover layer indicates a level of negative pressure below the cover layer.

The wound dressing apparatus of the preceding paragraph or in other embodiments can include one or more of the following features. The one or more apertures can be circular, rectangular, triangular, or oval shaped apertures. The one or more apertures can comprise circular shaped apertures between 3 mm to 7 mm in diameter. The one or more apertures in the absorbent layer can comprise an array of apertures. The array of apertures can comprise three apertures in the array. The one or more apertures can be positioned in a portion of the absorbent layer adjacent to the electronics assembly.

According to another embodiment, a wound dressing apparatus can comprise a wound contact layer comprising a proximal wound-facing face and a distal face, wherein the proximal wound-facing face is configured to be positioned in contact with a wound, an indicator material layer, and a cover layer configured to cover and form a seal over the wound contact layer and the indicator material layer, wherein the indicator material layer is configured to protrude relative to a surrounding surface of an upper surface of the wound dressing apparatus when negative pressure is applied to the wound dressing apparatus, and wherein the protruding indicator material layer indicates a level of negative pressure below the cover layer.

The wound dressing apparatus of the preceding paragraph or in other embodiments can include one or more of the following features. The indicator material layer can be configured to provide a visual or a tactile indication of negative pressure. The indicator material layer can have a shape selected from the group consisting of a rectangle, a semi-circle on a rectangle, a triangle, and a semi-circle. The indicator material layer can comprise a length that is less than the length of the cover layer. The indicator material layer can comprise a width that is less than the width of the cover layer. The indicator material layer can comprise an absorbent material. The wound dressing apparatus can further comprise a transmission layer comprising a proximal wound-facing face and a distal face, the transmission layer positioned above the distal face of the wound contact layer. The indicator material layer can comprise a width that is less than the width of the transmission layer. The indicator material layer can comprise a length that is less than the length of the transmission layer. The wound dressing apparatus can further comprise at least one absorbent layer. The indicator material layer can comprise a width that is less than the width of the at least one absorbent layer. The indicator material layer can comprise a length that is less than the length of the at least one absorbent layer. The at least one absorbent layer can comprise a first absorbent layer comprising a proximal wound-facing face and a distal face, and a second absorbent layer comprising a proximal wound-facing face and a distal face, the second absorbent layer positioned on the distal face of the first absorbent layer. The second absorbent layer can comprise the indicator material layer. The wound dressing apparatus can comprise an electronics area and an absorbent area, wherein the absorbent area is configured to be positioned over the wound and the electronics area is configured to receive an electronics assembly positioned underneath the cover layer. The wound dressing apparatus can further comprise a negative pressure source positioned underneath the cover layer in the electronics area. The indicator material layer can be positioned at a portion of the absorbent area adjacent to the electronics area. The indicator material layer can comprise an extension that extends from the electronics area into a portion of the absorbent area. The indicator material layer can be positioned within the absorbent area.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

FIGS. 2A-2B illustrate embodiments of an electronics unit incorporated into a wound dressing;

FIG. 3A illustrates an embodiment of wound dressing layers incorporating the electronic components within the wound dressing;

FIGS. 10A-10G illustrate embodiments of a wound dressing incorporating an electronics assembly and negative pressure indicators within the dressing layers;

DETAILED DESCRIPTION

Figure 1A:
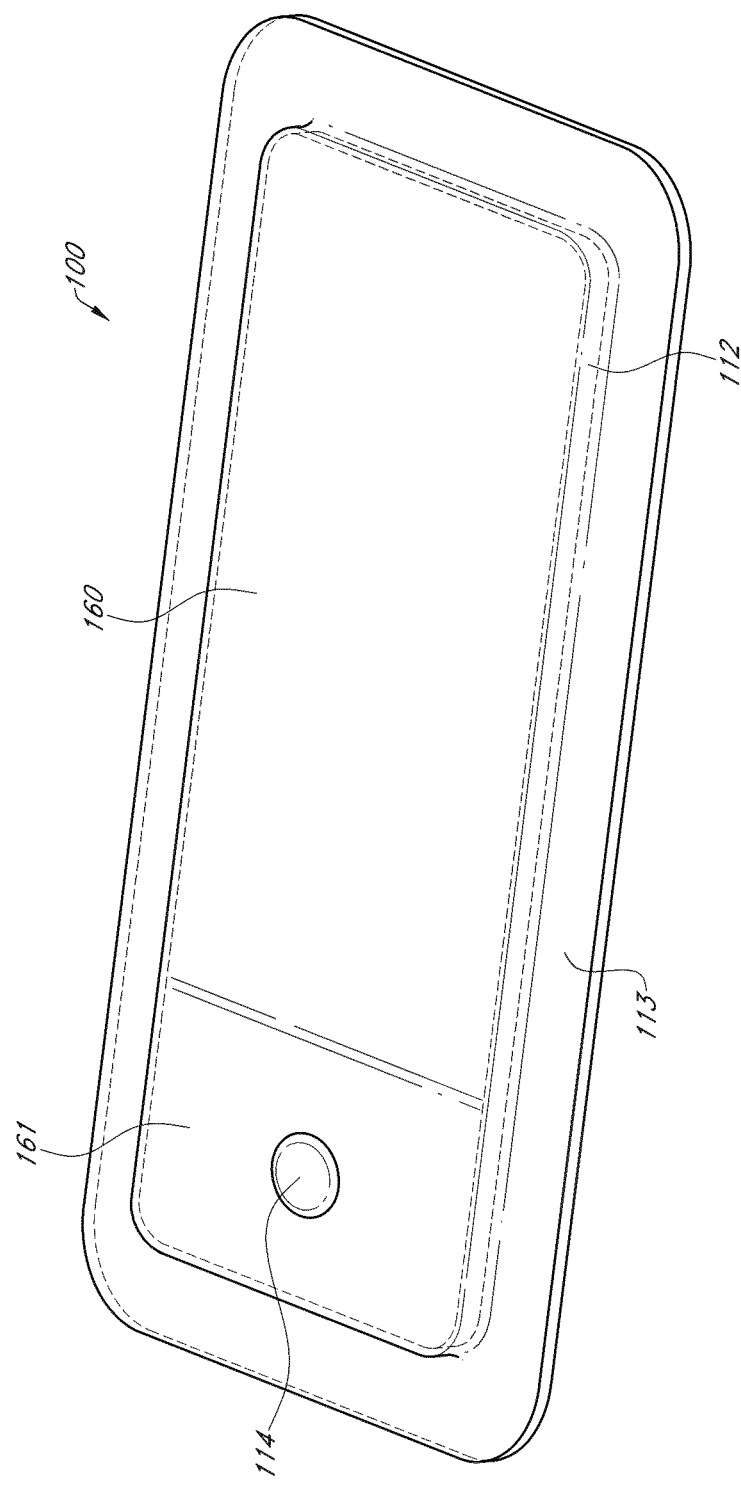
FIGS. 1A-1C illustrate a wound dressing incorporating the source of negative pressure and/or other electronic components within the wound dressing.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in International Application No. PCT/IB2013/001469, filed May 22, 2013, titled "APPARATUSES AND METHODS FOR NEGATIVE PRESSURE WOUND THERAPY," published as WO 2013/175306 on Nov. 28, 2013, U.S. patent application Ser. No. 14/418,874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. Application No. 2015/0182677, published Jul. 2, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as U.S. 2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

Embodiments of the wound dressings, wound treatment apparatuses and methods described herein relating to wound dressings with electronics incorporated into the dressing may also be used in combination or in addition to those described in PCT Application Number PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING," and which is hereby incorporated by reference in its entirety, including further details relating to embodiments of wound dressings, the wound dressing components and principles, and the materials used for the wound dressings.

Figure 1B:
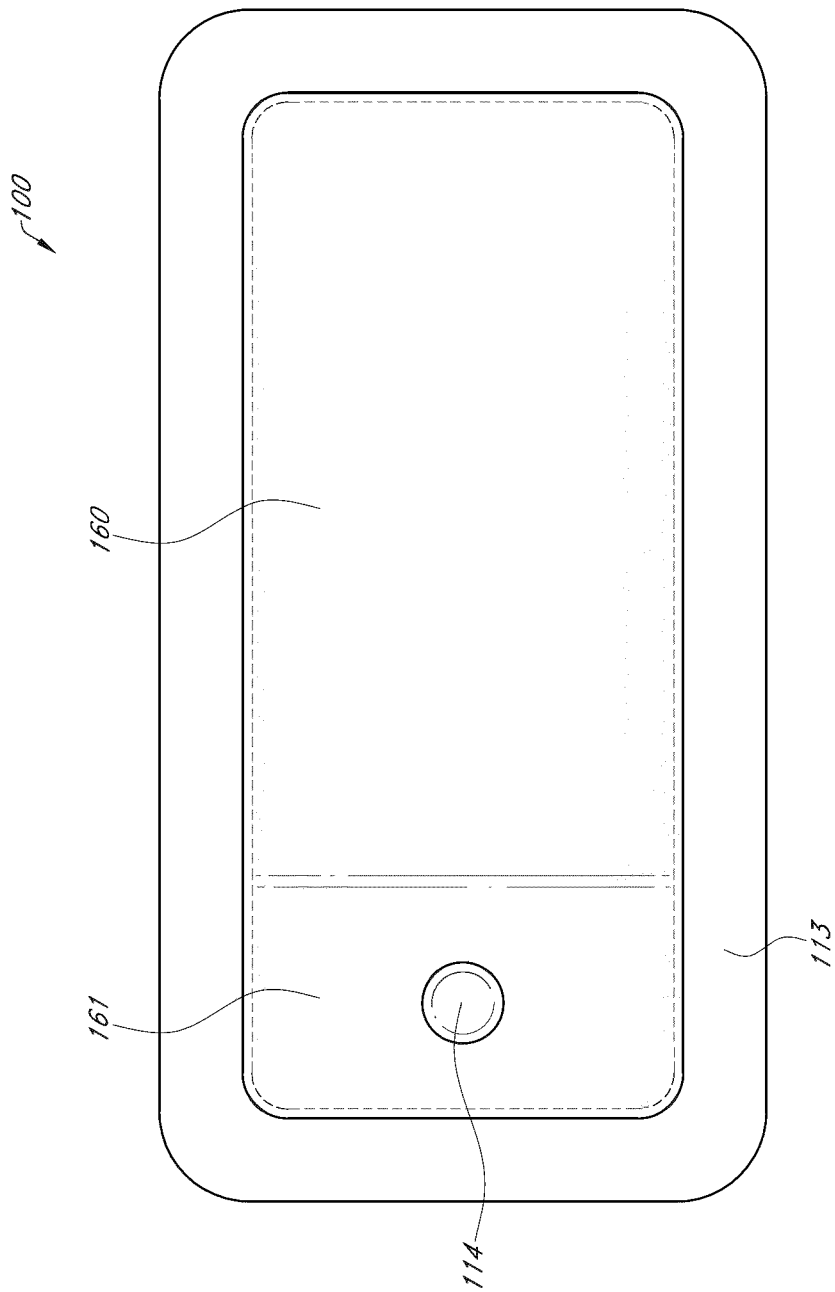
Figure 1C:
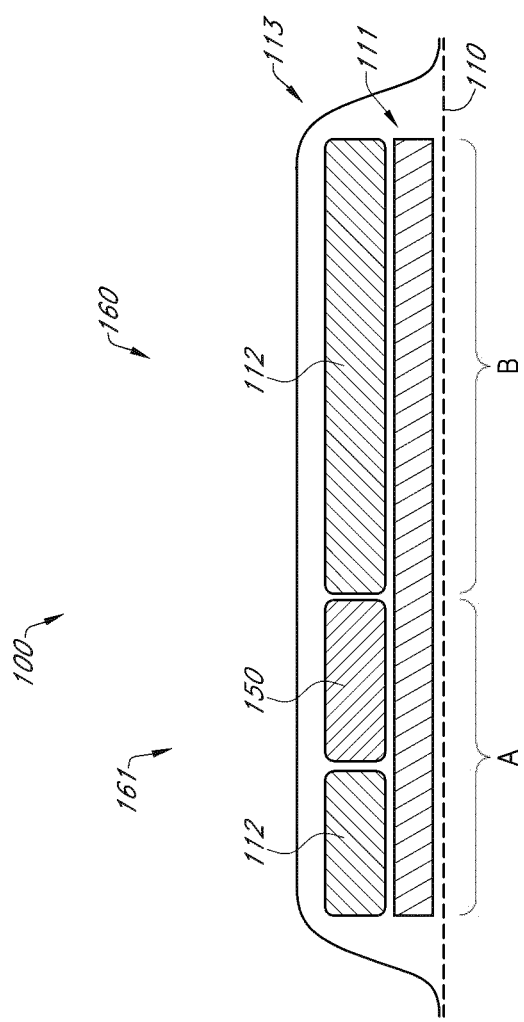

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include various material layers described here and described in further detail in International Application No. PCT/EP2017/055225, filed Mar. 6, 2017, entitled WOUND TREATMENT APPARATUSES AND METHODS WITH NEGATIVE PRESSURE SOURCE INTEGRATED INTO WOUND DRESSING. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. In some embodiments, the dressing can be provided as a single article with all wound dressing elements (including the pump) pre-attached and integrated into a single unit. In some embodiments, a periphery of the wound contact layer can be attached to the periphery of the cover layer enclosing all wound dressing elements as illustrated in FIG. 1A-1C.

In some embodiments, the pump and/or other electronic components can be configured to be positioned adjacent to or next to the absorbent and/or transmission layers so that the pump and/or other electronic components are still part of a single article to be applied to a patient. In some embodiments, with the pump and/or other electronics positioned away from the wound site. FIGS. 1A-1C illustrates a wound dressing incorporating the source of negative pressure and/or other electronic components within the wound dressing. FIGS. 1A-1C illustrates a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film or cover layer 113 positioned above the contact layer and other layers of the dressing. The wound dressing layers and components of the electronics area as well as the absorbent area can be covered by one continuous cover layer 113 as shown in FIGS. 1A-1C.

The dressing can comprise a wound contact layer 110, a transmission layer 111, an absorbent layer 112, a moisture vapor permeable film or cover layer 113, 113 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound.

The wound contact layer 110 can be a polyurethane layer or polyethylene layer or other flexible layer which is perforated, for example via a hot pin process, laser ablation process, ultrasound process or in some other way or otherwise made permeable to liquid and gas. The wound contact layer 110 has a lower surface and an upper surface. The perforations preferably comprise through holes in the wound contact layer 110 which enable fluid to flow through the layer 110. The wound contact layer 110 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 110 may help maintain the integrity of the entire dressing 100 while also creating an air tight seal around the absorbent pad in order to maintain negative pressure at the wound.

Some embodiments of the wound contact layer 110 may also act as a carrier for an optional lower and upper adhesive layer (not shown). For example, a lower pressure sensitive adhesive may be provided on the lower surface of the wound dressing 100 whilst an upper pressure sensitive adhesive layer may be provided on the upper surface of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized it may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

The transmission layer assists in distributing negative pressure over the wound site and facilitating transport of wound exudate and fluids into the wound dressing. In some embodiments, the transmission layer can be formed at least partially from a three dimensional (3D) fabric.

In some embodiments, the transmission layer 111 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 112 helps lock the liquid away or itself wicks the liquid onwards towards the cover layer 113 where it can be transpired.

Preferably, to improve the liquid flow across the transmission layer 111 (that is to say perpendicular to the channel region formed between the top and bottom spacer layers), the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Further, an absorbent layer (such as layer 112) for absorbing and retaining exudate aspirated from the wound can be utilized. In some embodiments, a superabsorbent material can be used in the absorbent layer 112. In some embodiments, the absorbent includes a shaped form of a superabsorber layer.

A layer 112 of absorbent material is provided above the transmission layer 111. The absorbent material, which comprise a foam or non-woven natural or synthetic material, and which may optionally comprise a super-absorbent material, forms a reservoir for fluid, particularly liquid, removed from the wound site. In some embodiments, the layer 111 may also aid in drawing fluids towards the cover layer 113.

The material of the absorbent layer 112 may also prevent liquid collected in the wound dressing from flowing freely within the dressing, and preferably acts so as to contain any liquid collected within the dressing. The absorbent layer 112 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 112 may typically be manufactured from ALLEVYN™ foam, Freudenberg 114-224-4 or Chem-Posite™11C-450. In some embodiments, the absorbent layer 112 may comprise a composite comprising superabsorbent powder, fibrous material such as cellulose, and bonding fibers. In a preferred embodiment, the composite is an airlaid, thermally-bonded composite.

In some embodiments, the absorbent layer 112 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

The wound dressing layers of the electronics area and the absorbent layer can be covered by one continuous cover layer or backing layer 113. As used herein, the terms cover layer and/or backing layer can be used interchangeably to refer to the layer of material in the dressing configured to cover the underlying dressing layers and seal to the wound contact layer and/or the skin surrounding the wound. In some embodiments, the cover layer can include a moisture vapor permeable material that prevents liquid exudate removed from the wound and other liquids from passing through, while allowing gases through.

The cover layer 113 is preferably gas impermeable, but moisture vapor permeable, and can extend across the width of the wound dressing 100. The cover layer 113, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer 113 and a wound site where a negative pressure can be established. The cover layer 113 is preferably sealed to the wound contact layer 110 in a border region around the circumference of the dressing, ensuring that no air is drawn in through the border area, for example via adhesive or welding techniques. The cover layer 113 protects the wound from external bacterial contamination (bacterial barrier) and allows liquid from wound exudates to be transferred through the layer and evaporated from the film outer surface. The cover layer 113 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the cover layer increases when the cover layer becomes wet. The moisture vapor permeability of the wet cover layer may be up to about ten times more than the moisture vapor permeability of the dry cover layer.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 114 as shown in FIGS. 1A-1B. The button or switch 114 can be used for operating the pump (e.g., turning the pump on/off).

The absorbent area 160 can include an absorbent material 112 and can be positioned over the wound site. The electronics area 161 can be positioned away from the wound site, such as by being located off to the side from the absorbent area 160. The electronics area 161 can be positioned adjacent to and in fluid communication with the absorbent area 160 as shown in FIGS. 1A-1C. In some embodiments, each of the electronics area 161 and absorbent area 160 may be rectangular in shape and positioned adjacent to one another. In FIG. 1C, the electronics area 161 is noted as area "A" and the absorbent area 160 is noted as area "B". In some embodiments, as illustrated in FIG. 1C, electronic components 150 can be positioned within a recess or cut out of the absorbent material 112 but off to the side of the absorbent area. As shown in the cross sectional view of the wound dressing layers in FIG. 1C, the absorbent material 112 can be positioned on both sides of the electronic components 150.

In some embodiments, additional layers of dressing material can be included in the electronics area 161, the absorbent area 160, or both areas. In some embodiments, the dressing can comprise one or more transmission or spacer layers and/or one or more absorbent layer positioned above the wound contact layer 110 and below the cover layer 113 of the dressing.

In some embodiments, the electronics area 161 of the dressing can comprise electronic components 150. In some embodiments, the electronics area 161 of the dressing can comprise one or more layers of transmission or spacer material and/or absorbent material and electronic components 150 can be embedded within the one or more layers of transmission or spacer material and/or absorbent material. The layers of transmission or absorbent material can have recesses or cut outs to embed the electronic components 150 within whilst providing structure to prevent collapse. The electronic components 150 can include a pump, power source, controller, and/or an electronics package.

A pump exhaust can be provided to exhaust air from the pump to the outside of the dressing. The pump exhaust can be in communication with the electronics area 161 and the outside of the dressing.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound. Also, as used herein, the upper surface or top surface refers to the surface of the dressing that is furthest from the surface of the skin or wound while the dressing is in use and positioned over the wound, and the bottom surface or lower surface refers to the surface of the dressing that is closest to the surface of the skin or wound while the dressing is in use and positioned over the wound.

FIG. 1A-1C illustrates a wound dressing apparatus incorporating the pump and/or other electronic components within the wound dressing and offset from the absorbent layer. In some embodiments, as shown in FIG. 1C, the absorbent area 160 comprises a transmission layer 111 positioned above the wound contact layer 110. An absorbent layer 112 can be provided above the transmission layer 111. In some embodiments, the electronics area 161 can include an electronics unit (shown in FIGS. 2A-2B). In some embodiments, the electronics unit is provided directly over the wound contact layer. In other embodiments, the electronics unit can be placed above a layer of wicking material, absorbent material, or transmission material that sits above the wound contact layer 110 of the dressing. For example, as shown in FIG. 1C, the electronics unit 150 may be positioned over the transmission layer 111. In some embodiments, the transmission layer 111 can be a single layer of material extending below the electronics unit 150 and the absorbent material 112. Thus, in some embodiments, the transmission layer 111 extends continuously through the absorbent area 160 and the electronics area 161. In alternative embodiments, the transmission layer below the electronics unit can be a different transmission layer than the transmission layer below the absorbent material 112. The transmission layer 111, absorbent material 112, and electronics unit 150 can be covered with a cover layer 113 that seals to a perimeter of the wound contact layer 110 as shown in FIGS. 1A-1C.

The electronics area 161 can include an electronics unit 150 positioned below the cover layer 113 of the dressing. In some embodiments, the electronics unit can be surrounded by a material to enclose or encapsulate a negative pressure source and electronics components by surrounding the electronics. In some embodiments, this material can be a casing. In some embodiments, the electronics unit can be encapsulated or surrounded by a protective coating, for example, a hydrophobic coating as described herein. The electronics unit can be in contact with the dressing layers in the absorbent area 160 and covered by the cover layer 113. As used herein, the electronics unit includes a lower or wound facing surface that is closest to the wound and an opposite, upper surface, furthest from the wound when the wound dressing is placed over a wound.

FIG. 1C illustrates an embodiment of a wound dressing incorporating an electronics unit 150 within the dressing. In some embodiments, the electronics sub assembly or electronics unit 150 can be embedded in an aperture or hole in an absorbent layer 112 towards one end of the dressing, as depicted in FIG. 1C.

In some embodiments, the absorbent components and electronics components can be overlapping but offset. For example, a portion of the electronics area can overlap the absorbent area, for example overlapping the superabsorber layer, but the electronics area is not completely over the absorbent area. Therefore, a portion of the electronics area can be offset from the absorbent area. The dressing layer and electronic components can be enclosed in a wound contact layer 110 positioned below the lower most layer and a cover layer 113 positioned above the absorbent layer 112 and electronics 150. The wound contact layer 110 and cover layer 113 can be sealed at a perimeter enclosing the dressing components. In some embodiments, the cover layer can be in direct physical contact with the absorbent material, and/or the electronics unit. In some embodiments, the cover layer can be sealed to a portion of the electronics unit and/or casing, for example, in areas where holes or apertures are used to accommodate the electronic components (e.g. a switch and/or exhaust).

FIGS. 2A-2B illustrate embodiments of an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more batteries 268. The electronics unit 267 can include a flexible circuit board 276 configured to be in electrical communication with the pump 272 and/or batteries 268.

As illustrated in FIG. 2A, the electronics unit 267 can include single button or switch 265 on the upper surface of the unit. The single button or switch 265 can be used as an on/off button or switch to stop and start operation of the pump and/or electronic components. The switch 265 can be a dome type switch configured to sit on the top of the pump. Because the switch is situated within the dressing the cover layer can be easily sealed around or over the switch. In some embodiments, the cover layer can have an opening or hole positioned above the switch. The cover layer can be sealed to the outer perimeter of the switch 265 to maintain negative pressure under the wound cover. The switch can be placed on any surface of the electronics unit and can be in electrical connection with the pump.

The electronics unit 267 can also include one or more vents or exhausts aperture 264 on the flexible circuit board for expelling the air exhausted from the pump. As shown in FIG. 2B, a pump outlet exhaust mechanism 274 can be attached to the outlet of the pump 272. The vent or exhaust aperture 264 can be in fluid communication with a pump exhaust mechanism 274 positioned at the outlet of the pump and extending to the lower surface of the flexible circuit board. In some embodiments, an exhaust vent 264 on the flexible circuit board can provide communication with the top surface of the dressing and allow the pump exhaust to be vented from the electronics unit. In some embodiments, the exhaust mechanism 274 can be attached to the outlet end of the pump and can extend out from the pump at a 90-degree angle from the pump orientation to communicate with the bottom surface of the flexible circuit board. In some embodiments, the exhaust mechanism 274 can include an antibacterial membrane and/or a non-return valve. In some embodiments, the exhaust vent 264 can include an antibacterial membrane and/or a non-return valve. The exhausted air from the pump can pass through the pump outlet and exhaust mechanism 274. In some embodiments, the cover layer 113 can include apertures or holes positioned above the exhaust vent 264 and/or membrane. The cover layer 113 can be sealed to the outer perimeter of the exhaust 264 to maintain negative pressure under the wound cover 113. In some embodiments, the exhausted air can be exhausted through the gas permeable material or moisture vapor permeable material of the cover layer. In some embodiments, the cover layer does not need to contain apertures or holes over the exhaust and the exhausted air is expelled through the cover layer. In some embodiments, the pump outlet mechanism 274 can be a custom part formed to fit around the pump as shown in FIG. 2B. The electronic unit 267 can include a pump inlet protection mechanism 280 as shown in FIG. 2C positioned on the portion of the electronic unit closest to the absorbent area and aligned with the inlet of the pump 272. The pump inlet protection mechanism 280 is positioned between the pump inlet and the absorbent area or absorbent layer of the dressing. The pump inlet protection mechanism 280 can be formed of a hydrophobic material to prevent fluid from entering the pump 272.

In some embodiments, the upper surface of the electronics unit can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (e.g. dressing leak, saturation level of the dressing, and/or low battery).

FIG. 2A-2B illustrates an embodiment of an electronics unit 267. The electronics unit 267 can include a pump 272 and one or more batteries 268 or other power source to power the pump 272 and other electronics. The pump can operate at about 27 volts or about 30 volts. The two batteries can allow for a more efficient voltage increase (6 volts to 30 volts) than would be possible with a single battery.

The batteries 268 can be in electrical communication with a flexible circuit board 276. In some embodiments, one or more battery connections are connected to a surface of the flexible circuit board 276. In some embodiments, the flexible circuit board can have other electronics incorporated within. For example, the flexible circuit board may have various sensors including, but not limited to, one or more pressure sensors, temperature sensors, optic sensors and/or cameras, and/or saturation indicators.

In such embodiments, the components of the electronics unit 267 may include a protective coating to protect the electronics from the fluid within the dressing. The coating can provide a means of fluid separation between the electronics unit 267 and the absorbent materials of the dressing. The coating can be a hydrophobic coating including, but not limited to, a silicone coating or polyurethane coating. In some embodiments, the electronics unit 267 can be encapsulated in a protective housing or enclosure as described in more detail herein. The pump inlet component or pump inlet protection mechanism can be used to protect the pump from fluid on the inlet and the pump outlet mechanism can include a non-return valve that protects fluid from entering the outlet as described in more detail with reference to PCT International Application No. PCT/EP2017/055225, filed Mar. 6, 2017, titled WOUND TREATMENT APPARATUSES AND METHODS WITH NEGATIVE PRESSURE SOURCE INTEGRATED INTO WOUND DRESSING and PCT International Application No. PCT/EP2017/059883, filed Apr. 26, 2017, titled WOUND DRESSINGS AND METHODS OF USE WITH INTEGRATED NEGATIVE PRESSURE SOURCE HAVING A FLUID INGRESS INHIBITION COMPONENT, which are hereby incorporated by reference in their entireties. The pump inlet component or pump inlet protection mechanism can be a component that inhibits fluid ingress. The pump inlet component or pump inlet protection mechanism can allow gas (e.g., air) but inhibit liquid (e.g., wound exudate) from passing through. The pump inlet component or pump inlet protection mechanism can be a porous structure that provides a plurality of flow paths between an interior of the wound dressing and the pump. The plurality of flow paths can inhibit occlusion (e.g., from wound exudate) of the pump. In some embodiments, the component can be made of or coated with a hydrophobic material that repels wound exudate, thereby inhibiting the ingress of fluid into the component and ultimately the pump.

The electronics unit 267 includes one or more slits, grooves or recesses 271 in the unit between the pump and the two batteries. The slits, grooves or recesses 271 can allow for the electronics unit 267 to be flexible and conform to the shape of the wound. The unit 267 can have two parallel slits, grooves or recesses 271 forming three segments of the electronics unit 267. The slits, grooves or recesses 271 of the unit 267 create hinge points or gaps that allows for flexibility of the electronics unit at that hinge point. The pump exhaust vent 264, switch 265, and indicator 266 are shown on the top surface of the electronics unit 267. As illustrated, one embodiment of the electronics unit 267 has two hinge points to separate the unit into three regions or panels, for example one to contain one battery, one to contain the pump, and one to contain another battery. In some embodiments, the slits, grooves or recesses may extend parallel with a longitudinal axis of the dressing that extends along the length of the dressing through the electronics area of the dressing through the absorbent area of the dressing.

FIG. 3A illustrates an embodiment of wound dressing layers incorporating the electronic components within the wound dressing. FIG. 3A illustrates a wound dressing with a wound contact layer 310 configured to contact the wound. The wound contact layer 310 can be a similar material and have a similar function as the wound contact layer described with reference to FIGS. 1A-1C. A transmission layer or spacer layer 311 is provided over the wound contact layer.

The transmission layer or spacer layer 311 can be a similar material and have a similar function as the transmission layer or spacer layer described with reference to FIGS. 1A-1C. The transmission layer 311 can assist in transmitting and distributing negative pressure over the wound site.

A first layer of apertured absorbent material 351 can be provided over the transmission layer 311. The first apertured absorbent layer 351 can include one or more apertures 329. In some embodiments, the apertures 329 can be sized and shaped to fit the electronics unit 350 therein. The first apertured absorbent layer 351 can be sized and shaped to the size of the electronics area and does not extend into the absorbent area. In some embodiments, the apertures 329 can be shaped and sized to fit the individual components of the electronics unit 350.

A second apertured absorbent layer 322 can be provided over the first absorbent layer 351. In some embodiments, the second absorbent layer 322 includes one or more apertures 328. The second absorbent layer 322 can be sized and shaped to the size of the electronics area and the absorbent area. In some embodiments, the apertures 328 can be shaped and sized to fit the individual components of the electronics unit 350. The first and second absorbent layers 351 and 322 can be a similar material and have a similar function as the absorbent layer described with reference to FIGS. 1A-1C.

An electronics unit 350 can be positioned in the apertures 328 and 329 of the first and second absorbent material 351 and 322. The electronics unit 350 can be similar to the electronics unit described with reference to FIGS. 2A-2B. The electronics unit 350 can include a pump 327, power source 326, and a printed circuit board 381. In some embodiments, the pump 327 can include a pump inlet mechanism 710 and an outlet mechanism 382. In some embodiments, the printed circuit board 381 can include electronics including but not limited to a switch, sensors, and LEDs as described herein. In some embodiments, the circuit board 381 can include one or more hole to be positioned over one or more exhaust vents (not shown) in the outlet mechanism 382 as described in more detail herein.

An overlay layer 317 can be provided over the electronics components 350 and absorbent layer 322. In some embodiments, the overlay layer 317 can be one or more layers of absorbent and/or transmission material as described herein. In some embodiments, the overlay layer 317 can comprise a conformable material overlaying and overbordering the perimeter of the lower layers of transmission and absorbent materials. In some embodiments, the overlay layer 317 can soften the edges of the wound dressing layers by decreasing the profile around the edges of the dressing layers. The overlay layer 317 can protect the cover layer from being punctured by the lower layers when the cover layer is sealed over the dressing layers below. The overlay layer 317 can include an aperture 371 to allow access to at least a portion of the electronics unit 350 positioned below.

A cover layer or backing layer 313 can be positioned over the overlay layer 317. The cover layer or backing layer 313 can be a similar material and have a similar function as the cover layer or backing layer described with reference to FIGS. 1A-1C. In some embodiments, when the overlay layer 317 is not used, the cover layer or backing layer 313 can be provided above absorbent layers 322, and/or electronic components 350. The cover layer 313 can form a seal to the wound contact layer 310 at a perimeter region enclosing the overlay layer 317, absorbent layers 322 and 351, electronic components 350, and the transmission layer 311. In some embodiments, the cover layer 313 can be a flexible sheet of material that forms and molds around the dressing components when they are applied to the wound. In other embodiments, the cover layer 313 can be a material that is preformed or premolded to fit around the dressing components as shown in FIG. 3A. As used herein, the terms cover layer and backing layer can be used interchangeably to refer to the layer of material in the dressing configured to cover the layers of the wound dressing.

In some embodiments, the cover layer or backing layer 313 can include an aperture 372. The aperture 372 can be positioned over at least a portion of the aperture 371 in the overlay layer 317 to allow access to at least a portion of the electronics unit 350 positioned below. In some embodiments, the apertures 371 and 372 can allow access to the switch and/or venting holes of the pump exhaust.

A label 341 can be provided over the apertures 371 and 372 and positioned over the exposed portion of the electronic components 350. The label can include the vent holes 342, indicator portions 344, and/or switch cover 343. The indicator portions 344 can include holes or transparent regions 344 for positioning over the one or more indicators or LEDs on the printed circuit board 381 below the label 341. The holes or transparent regions 344 can allow for the indicators or LEDs to be visible through the label 341. In some embodiments, the switch cover 343 can include a dome shaped cover positioned over the switch on the printed circuit board 381. In some embodiments, the label 341 can include embossed features for the switch cover 343. In some embodiments, the embossed features of the switch cover 343 can prevent accidental activation or deactivation of the device. In some embodiments, the switch or switch cover 343 can include a tab on the switch to prevent accidental activation or deactivation. The vent holes 342 of the label can allow exhaust from the pump outlet mechanism to pass through the label and exit the wound dressing to be exhausted to the atmosphere.

In some embodiments, the label can be positioned on top of the cover layer or backing layer 313. The label can seal to the cover layer to form a seal over the wound. In other embodiments, the label 341 can be positioned above the overlay layer 371 and below the cover layer or backing layer 313. In such embodiments, the cover layer 313 can have one or more apertures over one or more components of the label 341. For example, the cover layer 313 can have apertures over the vent holes 342, indicator portions 344, and/or switch cover 343.

Figure 3B:
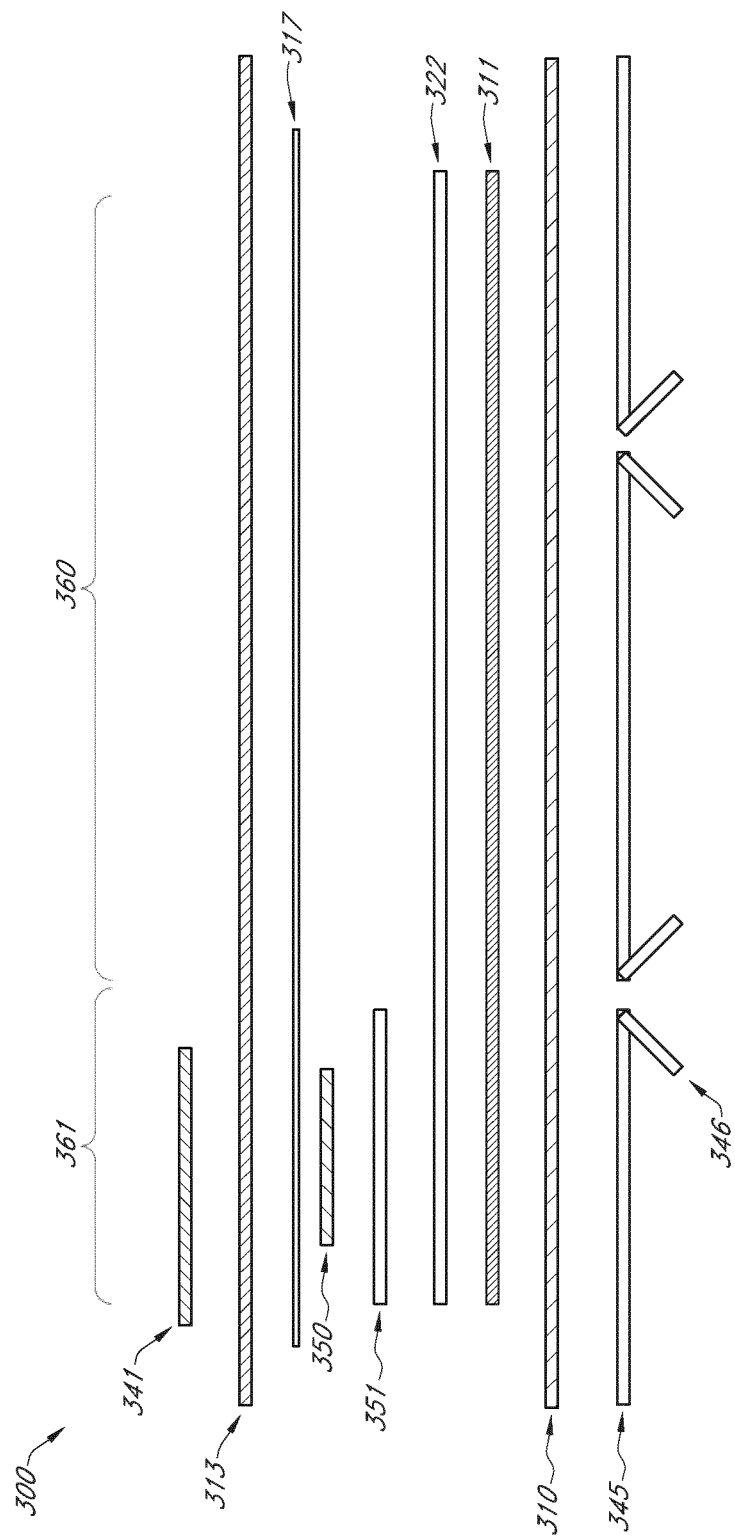
FIG. 3B illustrates a cross sectional layout of the material layers of the wound dressing incorporating an electronics assembly within the dressing.

FIG. 3B illustrates a cross sectional layout of the material layers of the wound dressing incorporating an electronics assembly within the dressing. The dressing 300 included multiple material layers and an electronics assembly 350. The electronics assembly 350 is shown with the electronic components assembled into a single unit. The wound dressing 300 can include an electronics area 361 including the electronics and an absorbent area or dressing area 360 that is intended to be applied to the wound as described with reference to FIGS. 1A-1C.

As described herein, the one or more material layers can extend into both the electronics area 361 and the dressing area 360. The dressing 300 can include a wound contact layer 310, transmission layer 311, absorbent layers 322 and 351, an overlay layer 317, and a cover or backing layer 313 as illustrated in FIG. 3B. The absorbent layers 322 and 351 can include recesses or cutouts to receive the components of the electronics assembly 350 as described herein. In some embodiments, as illustrated in FIG. 3B the small apertured absorbent layer 351 can be positioned on top of the large apertured absorbent layer 322. In other embodiments, as illustrated in FIG. 3A the small apertured absorbent layer 351 can be positioned on below of the large apertured absorbent layer 322.

In some embodiments, the overlay layer 317 and/or the cover layer 313 can include a cut out or aperture positioned over the switch and/or indicators of the electronics assembly 350. A label or covering 341 can be positioned to over at least a portion of the electronics assembly 350 and any cutouts in the overlay layer 317 and/or the cover layer 313. The label or covering 341 can be similar to the label or covering 341 as described previously with reference to FIG. 3A.

Before use, the dressing can include a delivery layer 345 adhered to the bottom surface of the wound contact layer. The delivery layer 345 can cover adhesive or apertures on the bottom surface of the wound contact layer 310. In some embodiments, the delivery layer 345 can provided support for the dressing and can assist in sterile and appropriate placement of the dressing over the wound and skin of the patient. The delivery layer 345 can include handles 346 that can be used by the user to separate the delivery layer 345 from the wound contact layer 310 before applying the dressing 300 to a wound and skin of a patient.

Figure 3C:
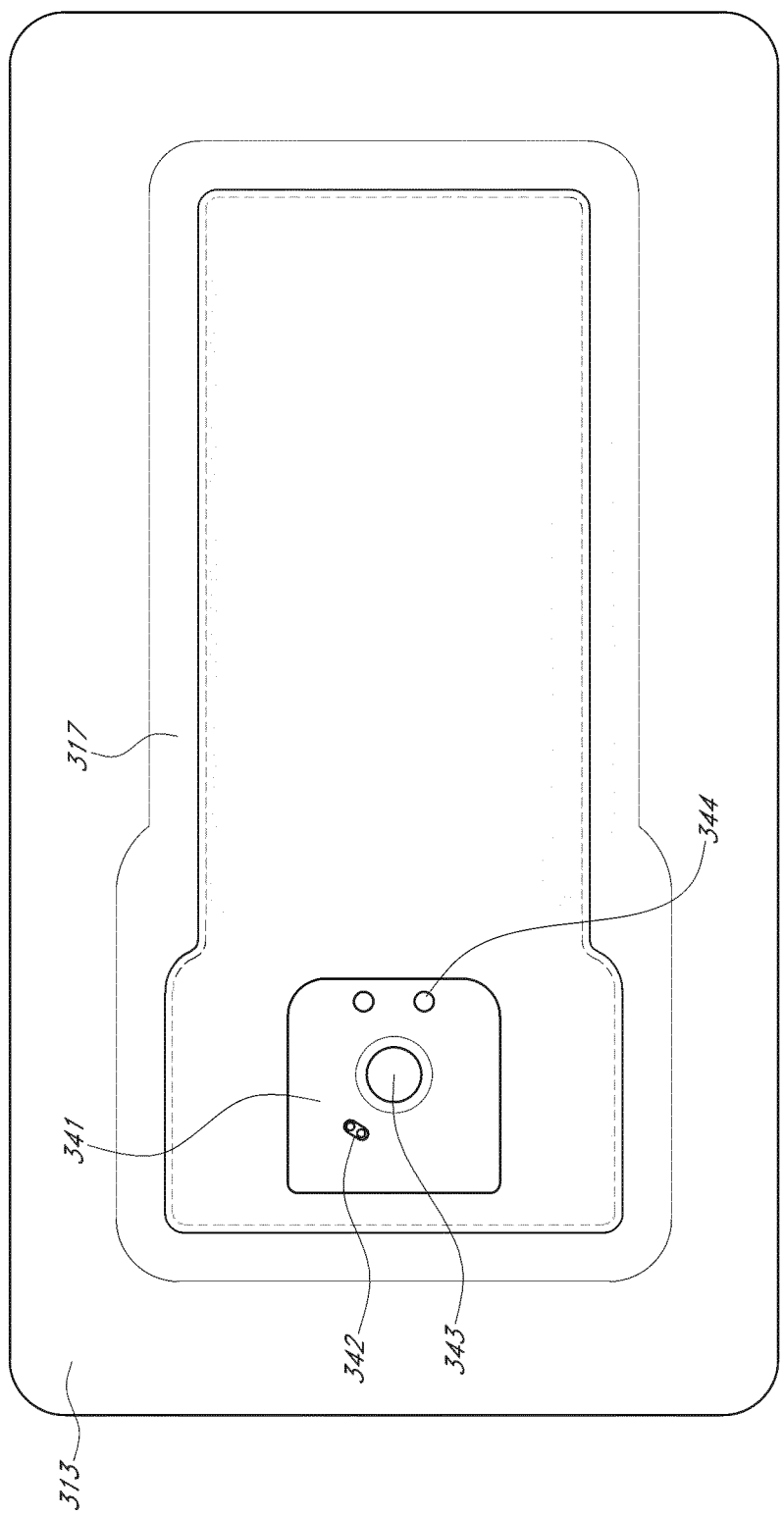
FIG. 3C illustrates a top view of an embodiment of the wound dressing incorporating an electronic assembly within the dressing.

FIG. 3C illustrates a top view of an embodiment of the wound dressing incorporating an electronic assembly within the dressing.

FIG. 3C shows a cover layer 313 and electronics covering 341 covering the overlay layer 317 and underlying dressing and electronics components. The cover layer 313 can seal to the wound contact layer 310 at a perimeter region of the wound contact layer 310. In some embodiments, the label or electronics covering 341 can be positioned over the cover layer 313. In other embodiments, the cover layer 313 can seal over the electronics covering 341. In some embodiments, the cover layer 313 can include one or more holes in the cover layer 313 positioned over the switch and/or pump outlet vent(s). In some embodiments, the cover layer 313 can include a single hole that is positioned over the switch cover 343, visual indicators 344, and/or pump outlet vent(s) 342 in the covering or label 341 as shown in FIG. 3C. In some embodiments, the label can include embossed features for the switch cover 343. In some embodiments, the embossed features of the switch cover 343 can prevent accidental activation or deactivation of the device. In some embodiments, the switch or switch cover 343 can include a tab on the switch to prevent accidental activation or deactivation.

The visual indicators 344 can provide an indication of operation of the negative pressure source and/or an indication of the level of negative pressure that is applied to the wound. In some embodiments, the visual indicators can include one or more light sources or LEDs. In some embodiments, the visual indicator light sources an illuminate to indicate a condition or change of condition. In some embodiments, the light source can illuminate in a particular sequence and/or color that indicates a condition. For example, in some embodiments, the light source can flash to notify the user that the device is operating properly. In some embodiments, the light source can automatically flash periodically and/or the light source can be activated by the switch or other button to light up and indicate a condition.

In some embodiments, the switch can be pressed and/or held down to power the dressing and electronics on and off. In some embodiments, once the switch is activated and the pump and associated colored LED, for example, green colored LED, can be used to confirm the dressing and integrated negative pressure source are operational. In some embodiments, during operation of the pump and dressing, the pump and dressing can enter the fault state indicated by a colored LED, for example, orange colored LED.

Electronic Assembly

The wound dressing described herein can utilize the embedded electronic assembly to generate negative pressure under the dressing. However, it can be important to protect the assembly from wound exudate or other bodily fluids that would corrode the electronics. It can also be important to protect the patient from the electric and electronic components. The electronics assembly can incorporate a pump that pull air from the dressing and exhaust to the environment in order to produce the required negative pressure differential. Therefore, it can be difficult to protect the electronics assembly and allow fluid communication between the electronic assembly and the dressing and environment surrounding the dressing. For example, complete encapsulation or potting of the assembly could prevent the movement of air from the dressing and atmosphere to the pump. In some embodiments, described previously herein, the electronic components of the electronics assembly can be protected from the environment by partial encapsulation, potting, and/or a conformable coating. In some embodiments, potting of electronic components can include a process of filling a complete electronic assembly with a solid or gelatinous compound for resistance to shock and vibration, exclusion of moisture, and/or exclusion of corrosive agents.

Figure 4A:
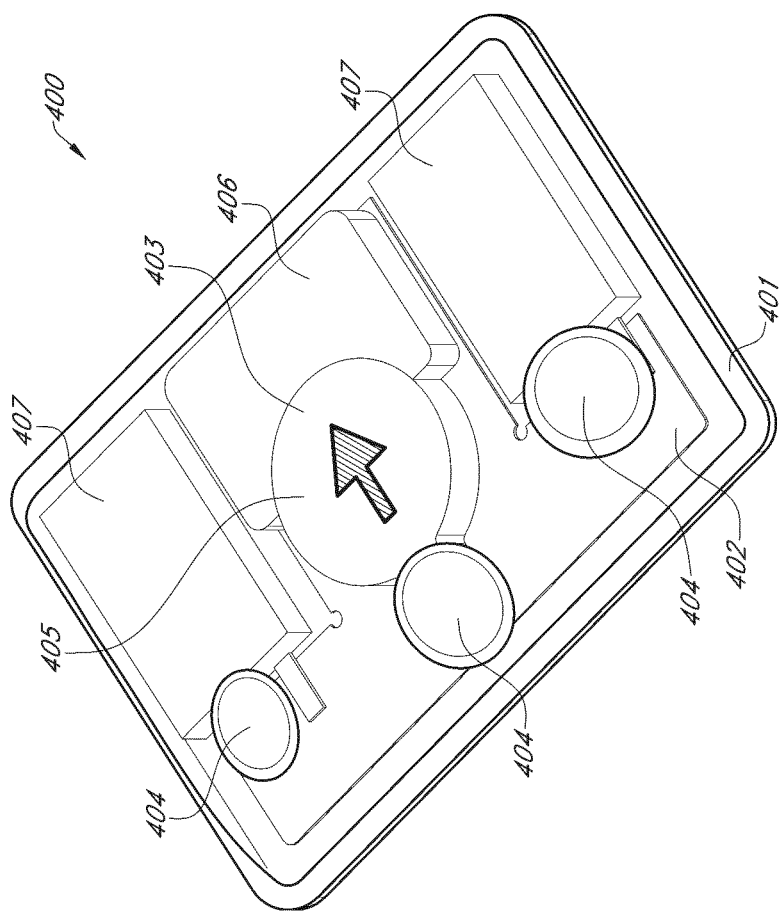
FIGS. 4A and 4B illustrate an embodiment of a housing of the electronics assembly enclosing the electronics unit within.
Figure 4B:
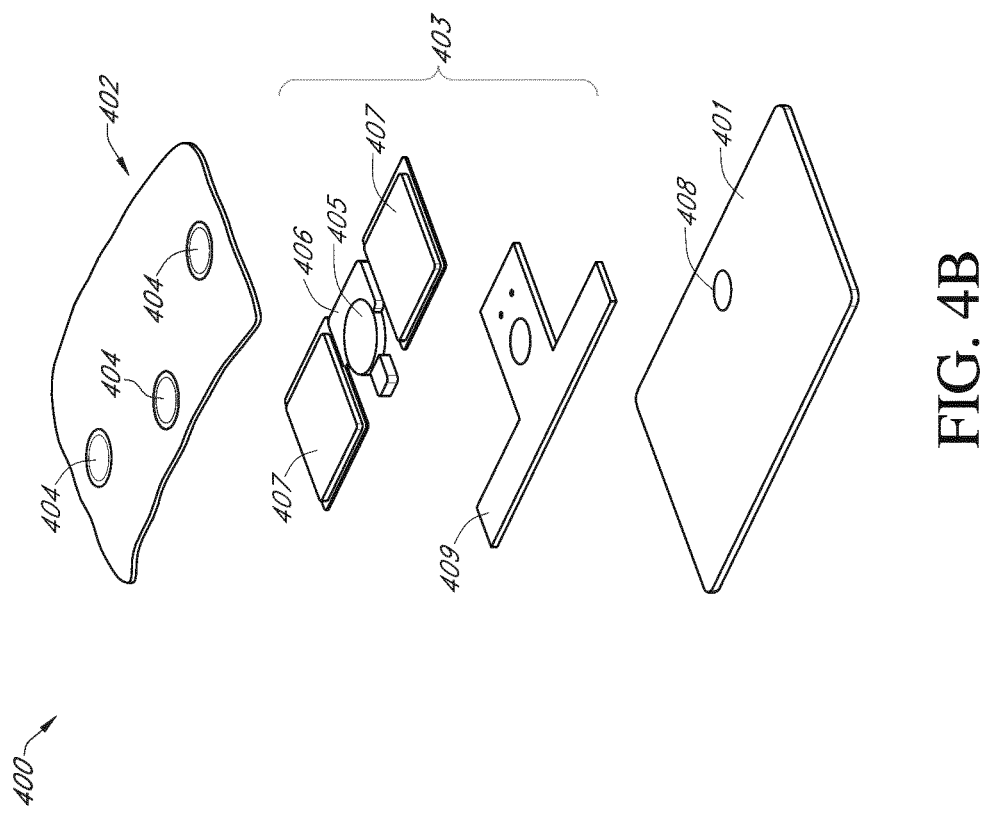

An electronics assembly can be used that includes an electronics unit positioned within an enclosure or housing, as illustrated in FIG. 4A, to be incorporated into a wound dressing. The electronics unit enclosed in the housing can be similar to the electronics unit described with reference to FIGS. 2A-2B but the electronics unit can be positioned within an enclosure or housing. The housing with the electronics unit enclosed within can be placed in the dressing. FIGS. 4A-4B illustrate an embodiment of an electronics assembly 400 enclosing an electronics unit 403 within a housing.

As illustrated in FIGS. 4A and 4B, the housing of the electronics assembly 400 can include a plate 401 and flexible film 402 enclosing the electronics unit 403 within. The electronics unit 403 can include a pump 405, inlet protection mechanism 410 (shown in FIG. 4B), pump exhaust mechanism 406, power source 407, and flexible circuit board 409. In some embodiments, the electronics unit 403 and pump 405 can be used without the inlet protection mechanism 410. The flexible film 402 can be attached to the plate 401 by welding (heat welding) or adhesive bonding to form a fluid tight seal and enclosure around the electronic components. In some embodiments, the flexible film 402 can be attached to the plate at a perimeter of the plate by heat welding, adhesive bonding, ultrasonic welding, RF welding, or any other attachment or bonding technique.

The flexible film 402 can be a flexible plastic polymeric film. In some embodiments, the flexible film 402 can be formed from any material flexible polymeric film or any flexible material that confirms around the electronics. The flexible film can maintain conformability and flexibility while protecting and insulating the components within. In some embodiments, the flexible film 402 can be formed from a flexible or stretchable material, such as one or more of polyurethane, thermoplastic polyurethane (TPU), silicone, polycarbonate, polyethylene, methylated polyethylene, polyimide, polyamide, polyester, polyethelene tetraphthalate (PET), polybutalene tetreaphthalate (PBT), polyethylene naphthalate (PEN), polyetherimide (PEI), along with various flruopolymers (FEP) and copolymers, or another suitable material. In some embodiments, the flexible film 402 can be formed from polyurethane.

The plate 401 can be a plastic polymer plate. In some embodiments, the plate can be a flexible material to allow conformability to movement or flexing of the dressing when it is applied to a wound. In some embodiments, the plate can be integrated with the components of the label described with reference to FIGS. 3A-3C. In other embodiments, the label can be a separate component attached to the top surface of the plate 401.

The flexible film 402 and plate 401 can be waterproof to protect the electronics unit 403 from fluid within the dressing. In some embodiments, the flexible film 402 can be sized appropriately so as not to limit the flexibility of the assembly. In some embodiments, depending on the properties of the film 402, the electronics assembly 400 can be thermoformed or vacuum formed to assist in the function of maintaining the flexibility of the assembly. In some embodiments, the electronics unit 403 can be bonded or adhered to the plate 401 within the housing such that the electronics unit 403 cannot move within.

In some embodiments, the housing can include one or more windows 404. The windows 404 can be a porous film or membrane that can allow gas to pass through. The windows 404 can be a hydrophobic film or membrane. In some embodiments, the hydrophobic nature of the window 404 can repel wound fluids and prevent the leak of fluids into the electronics assembly 400. In some embodiments, the windows 404 can include a bacterial filter. In some embodiments, the windows 404 can have the porosity that enables them to act as a bacterial filter and preventing bacterial release from the body fluids into the environment. The windows 404 can also prevent the ingress of bacteria from the environment to the wound site.

The electronics assembly 400 can have more than one window 404 or a larger window 404 to provide a sufficiently large area for air movement therethrough, thus minimizing the pressure drop across the membrane and hence the power consumption of the system in achieving the pressure differential. In some embodiments, as illustrated in FIGS. 4A-4B, the electronics assembly 400 can include several windows with a small area. In other embodiments, the electronics assembly can include a window with a single large area.

The electronics assembly 400 illustrated in FIGS. 4A-4B can be incorporated within the wound dressing such that, once the dressing is applied to the body of the patient, air from within the dressing can pass through the windows 404 to be pumped out in the direction shown by the arrow on the pump 405. The exhausted air from the pump can pass out of the pump assembly through the pump exhaust mechanism 406 and be exhausted or vented from the housing of the electronics assembly 400 through an aperture or vent 408 in the plate 401. In some embodiments, the flexible circuit board 409 can be positioned between the exhaust mechanism 406 and the plate 401. The flexible circuit board 409 can also include an aperture or vent aligned with the exhaust hole in the exhaust mechanism as described with reference to FIGS. 2A-2B. The vent hole or apertures in the exhaust mechanism 406, flexible circuit board 409, and plate 401 can be aligned and sealed to each other. This seal can ensure the pump exhaust is exhausted from the electronics assembly 400 through the vent 408 in the plate 401. In other embodiments, the exhaust mechanism 406 of the electronics unit 403 can be positioned on and bonded directly to the plate 401 with an air tight seal.

The top side of the plate 401 (not shown in FIGS. 4A-4B) can include a label similar to the label described with reference to FIGS. 3A-3C. In other embodiments, the top side of the plate 401 can integrate the components of the label described with reference to FIG. 3A-3C within the plate 401. In such embodiments, a separate label is not needed. For example, in addition to the vent holes, the plate 401 can include the indicator portions and/or a switch cover described previously herein.

In some embodiments, the electronics assembly 400 can be embedded within the wound dressing in the same manner as the electronics unit described with reference to FIGS. 3A-3C. The dressing can have one or more absorbent layers within the dressing and the absorbent layers can have a single aperture or recess for receiving the electronics assembly within. In some embodiments, the electronics assembly can be positioned below the overlay layer similar to the electronics unit described with reference to FIGS. 3A-3C. In such embodiments, the overlay layer would include an aperture to allow access to at least a portion of the top surface of the plate 401.

When the electronics assembly 400 is positioned within the dressing it can be positioned below the wound cover and the overlay layer similar to the electronics unit described with reference to FIGS. 3A-3C. In other embodiments, an overlay layer is not used and the electronics assembly 400 is positioned directly below the cover layer or backing layer.

The cover layer or backing layer can include an aperture exposing a portion of, most of, or all of the top surface of the plate 401. The aperture in the cover layer can be positioned over at least a portion of the plate 401 to allow access to at least a portion of the plate 401 positioned below the cover layer. In some embodiments, the cover layer can have a plurality of apertures over one or more components of the label or top surface of the plate 401. For example, the cover layer can have apertures over the vent holes, indicator portions, and/or switch cover. In other embodiments, the cover layer can have a single aperture over the one or more components of the label or top surface of the plate 401 including but not limited to the vent holes, indicator portions, and/or switch cover.

When a separate label is used, it can be applied to the dressing and exposed portion of the plate 401 as described with reference to FIG. 3A-3C, above or below the cover layer.

Figure 5A:
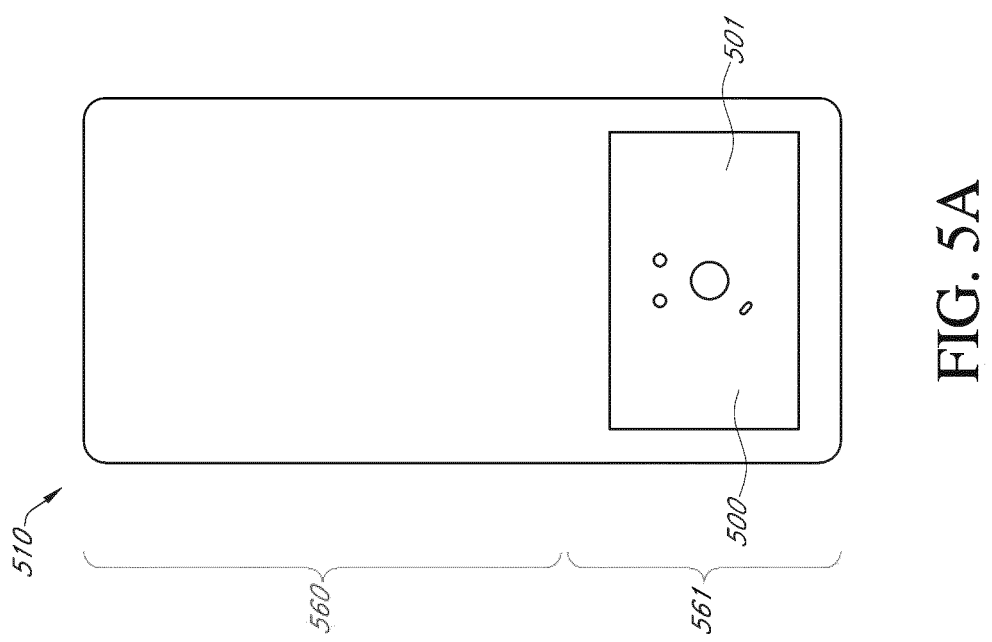
FIGS. 5A-5B illustrate embodiments of the electronics assembly positioned within an aperture in wound dressing layers.
Figure 5B:
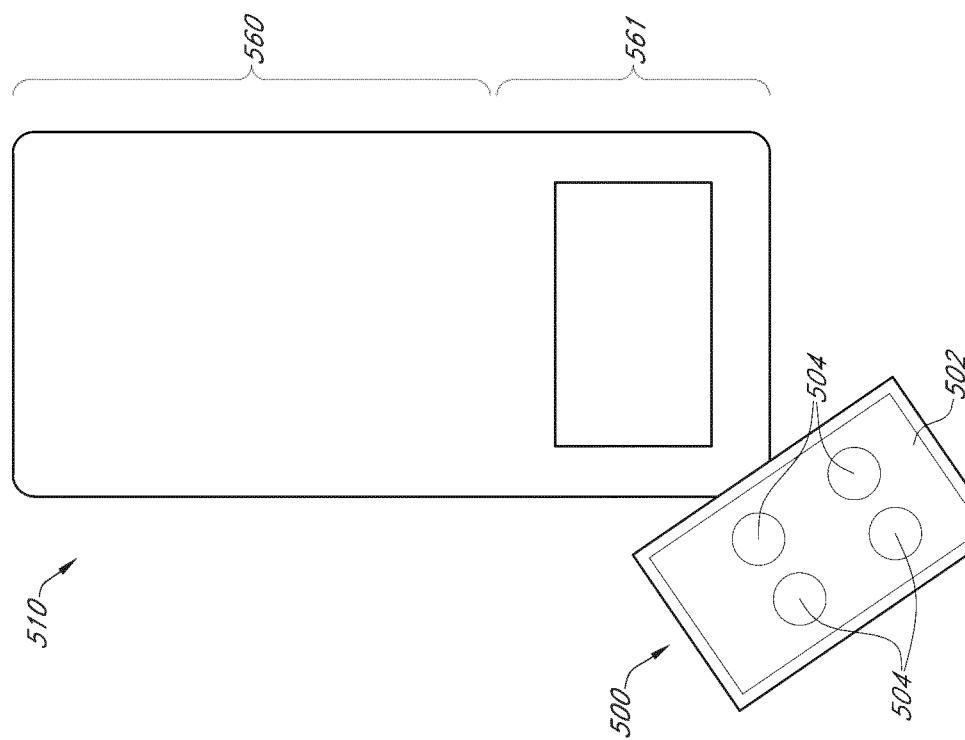

FIGS. 5A-5B illustrate embodiments of the electronics assembly 500 positioned within an aperture in wound dressing 510 layers. As illustrated in FIGS. 5A-5B, the dressing 510 can include an absorbent area 560 and an electronics area 561 similar to the corresponding components described with reference to FIGS. 1A-1C and 3A-3C. The dressing can have one or more dressing layers similar to the layers described with reference to FIGS. 1A-1C and 3A-3C. The dressing layers can have a single aperture or recess for receiving the electronics assembly within.

The wound dressing 510 can be formed from a wound contact layer, a transmission layer, and one or more absorbent layers as shown in FIGS. 1A-C and 3A-3C. The one or more absorbent layers can have a single aperture to receive the electronics assembly 500. The transmission layer and one or more absorbent materials can be covered with a cover layer 513 that seals to a perimeter of the wound contact layer as described with reference to FIGS. 1A-1C. As illustrated in FIGS. 5A-5B, the overlay layer is not used. The aperture in the one or more absorbent layers can be aligned with the aperture 520 in the cover layer 513.

FIG. 5A illustrates a top view of the electronics assembly 500 positioned in an electronics area 561 of the dressing 510. FIG. 5A illustrates a cover layer 513 of the dressing 510 with an electronics assembly 500 positioned in a recess in the dressing. The other layers of the wound dressing below the cover layer are not shown. The electronics assembly 500 can be similar to the electronics assembly described with reference to FIGS. 4A-4B. The electronics assembly 500 can include an electronics unit enclosed within a housing including a plate 501 and a flexible film 502. The plate 501 shown in FIG. 5A can include the features of the label including the one or more vents 542, one or more indicator portions 544, and/or a button or switch 543. FIG. 5B illustrates an embodiment of the electronics assembly 500 removed from the electronics area 561 of the dressing 510. The electronics assembly 500 is shown upside down with the windows facing up.

The electronics assembly can have a first side positioned on the wound facing side of the electronics assembly 500 when the dressing 510 is positioned over the wound. As illustrated, the flexible film 502 and windows 504 can form the first wound facing side of the electronics assembly 500 in contact with the dressing layer and facing the wound when the dressing is positioned over the wound. The electronics assembly 500 can have a second side opposite the first side. The plate 501 can form the second side of the electronics assembly and can be in contact with the environment when the dressing is positioned over the wound.

As illustrated in FIG. 5B, the flexible film 502 can have windows 504. When the electronics assembly 500 is positioned on or in the wound dressing as shown in FIG. 5A, the windows 504 are in fluid communication with the layers within the wound dressing allowing the electronics assembly to generate negative pressure under the dressing 510.

Figure 6:
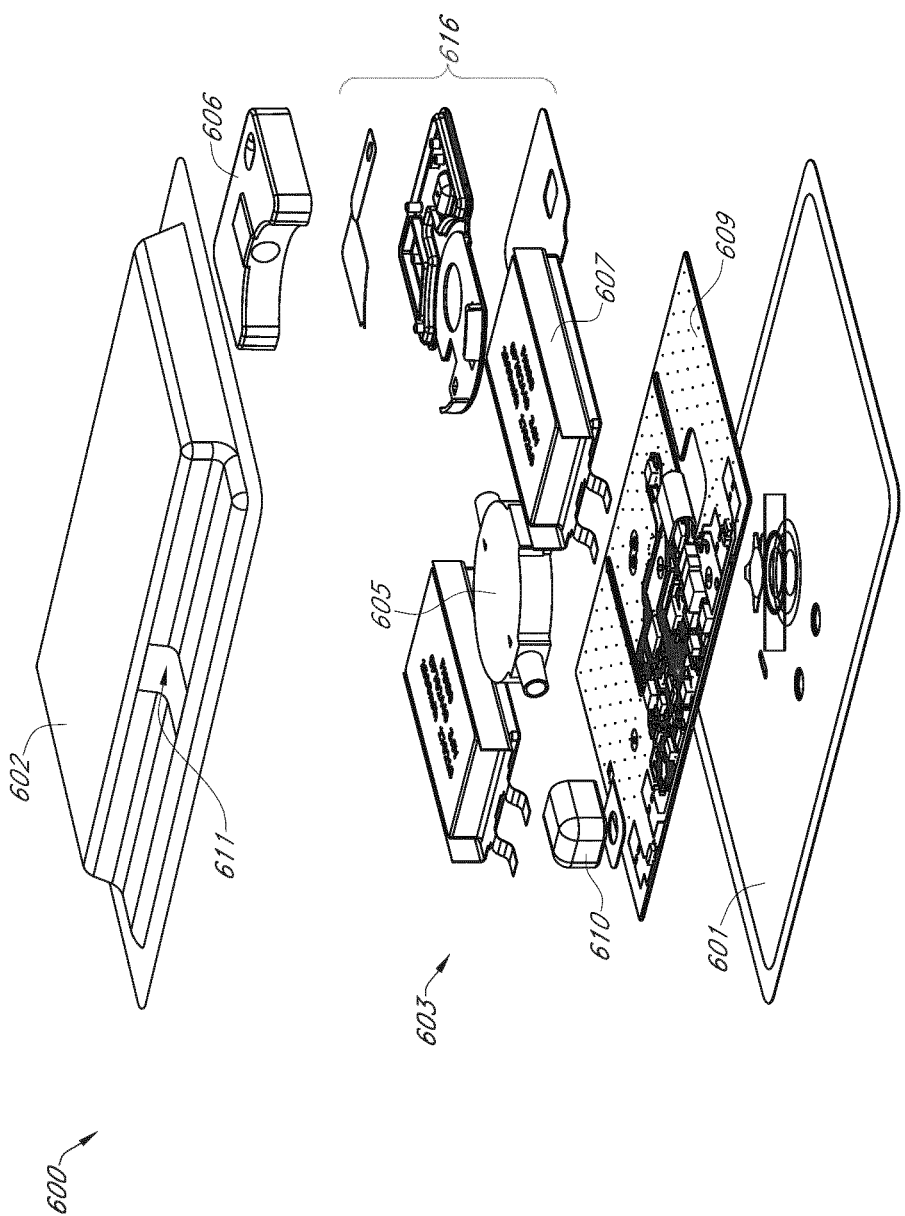
FIG. 6 is an exploded perspective view of an embodiment of an electronics assembly enclosing an electronics unit within a housing.

FIG. 6 illustrates an embodiment of an electronics assembly 600 enclosing an electronics unit within a housing. As illustrated in FIG. 6, the housing of the electronics assembly 600 can include a plate 601 and flexible film 602 enclosing the electronics unit 603 within. The electronics unit 603 can include a pump 605, inlet protection mechanism 610, pump exhaust mechanism 606, power source 607, and flexible circuit board 609.

The pump exhaust mechanism 606 can be similar to the pump exhaust mechanism 406. However, the pump exhaust mechanism 606 and the pump 605 can sit within an extended casing 616.

The flexible film 602 can be attached to the plate 601 by welding (heat welding) or adhesive bonding to form a fluid tight seal and enclosure around the electronic components. In some embodiments, the flexible film 602 can be attached to the plate at a perimeter of the plate by heat welding, adhesive bonding, ultrasonic welding, RF welding, or any other attachment or bonding technique.

The flexible film 602 can be a flexible plastic polymeric film. In some embodiments, the flexible film 602 can be formed from any material flexible polymeric film or any flexible material that confirms around the electronics. The flexible film can maintain conformability and flexibility while protecting and insulating the components within. In some embodiments, the flexible film 602 can be formed from a flexible or stretchable material, such as one or more of polyurethane, thermoplastic polyurethane (TPU), silicone, polycarbonate, polyethylene, methylated polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. In some embodiments, the flexible film 602 can be formed from polyurethane.

The plate 601 can be a plastic polymer plate. In some embodiments, the plate can be a flexible material to allow conformability to movement or flexing of the dressing when it is applied to a wound. In some embodiments, the plate can be integrated with the components of the label described with reference to FIGS. 3A-3C. In other embodiments, the label can be a separate component attached to the top surface of the plate 601. In some embodiments, the plate and/or label can have a larger surface area than the flexible circuit board and/or the electronics unit so that the flexible film 602 can seal to the outer perimeter of the plate and/or label around the flexible circuit board and/or the electronics unit The flexible film 602 and plate 601 can be waterproof to protect the electronics unit 603 from fluid within the dressing. In some embodiments, the flexible film 602 can be sized appropriately so as not to limit the flexibility of the assembly. In some embodiments, depending on the properties of the film 602, the electronics assembly 600 can be thermoformed or vacuum formed to assist in the function of maintaining the flexibility of the assembly. In some embodiments, the electronics unit 603 can be bonded or adhered to the plate 601 within the housing such that the electronics unit 603 cannot move within.

In some embodiments, the flexible film 603 can include an aperture 611. The aperture 611 can allow the inlet protection mechanism 610 to be in fluid communication with the absorbent and/or transmission layers of the wound dressing. The perimeter of the aperture 611 of the flexible film 603 can be sealed or attached to the inlet protection mechanism 610 by welding (heat welding) or adhesive bonding to form a fluid tight seal and enclosure around the inlet protection mechanism 610 allowing the electronic components 603 to remain protected from fluid within the dressing. In some embodiments, the flexible film 602 can be attached to the inlet protection mechanism 610 at a perimeter of the inlet protection mechanism 610 by heat welding, adhesive bonding, ultrasonic welding, RF welding, or any other attachment or bonding technique. The inlet protection mechanism 610 can prevent wound exudate or liquids from the wound and collected in the absorbent area 660 of the wound dressing from entering the pump and/or electronic components of the electronics assembly 600.

The electronics assembly 600 illustrated in FIG. 6 can be incorporated within the wound dressing such that, once the dressing is applied to the body of the patient, air from within the dressing can pass through the inlet protection mechanism 610 to be pumped out toward the pump exhaust mechanism 606 in communication with an aperture in the casing 616 and flexible circuit board 609 as described herein.

In some embodiments, the casing 616 can include an aperture or vent to allow the air exhausted from the pump exhaust mechanism 606 to pass through. The exhausted air from the pump can pass out of the pump assembly through the pump exhaust mechanism 606 and casing 616 and be exhausted or vented from the housing of the electronics assembly 600 through an aperture or vent in the plate 601. In some embodiments, the flexible circuit board 609 can be positioned between the exhaust mechanism 606 and the plate 601. The flexible circuit board 409 can also include an aperture or vent aligned with the exhaust hole in the exhaust mechanism as described with reference to FIGS. 2A-2B. The vent hole or apertures in the exhaust mechanism 606, casing 616, flexible circuit board 609, and plate 601 can be aligned and sealed to each other. This seal can ensure the pump exhaust is exhausted from the electronics assembly 600 through the vent in the plate 601. In other embodiments, the exhaust mechanism 606 of the electronics unit 603 can be positioned on and bonded directly to the plate 601 with an air tight seal.

The top side of the plate 601 (not shown in FIG. 6) can include a label similar to the label described with reference to FIGS. 3A-3C. In other embodiments, the top side of the plate 601 can integrate the components of the label described with reference to FIG. 3A-3C within the plate 601. In such embodiments, a separate label is not needed. For example, in addition to the vent holes, the plate 601 can include the indicator portions and/or a switch cover as described herein.

FIGS. 7A-7D show a lower wound facing surface of an electronics assembly 700. FIGS. 7A-7D illustrate embodiments of an electronics assembly including a pump inlet protection mechanism 710 sealed to the exterior of the flexible film 702 as described herein with reference to FIG. 6.

Figure 7A:
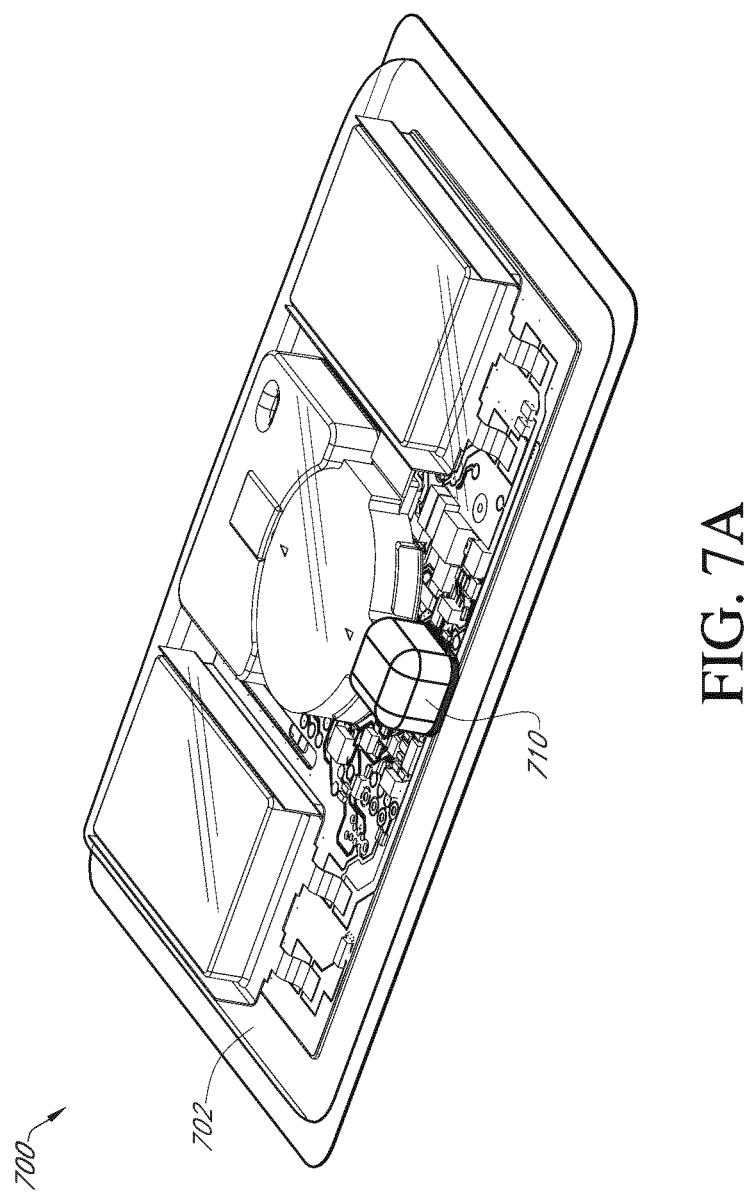
FIG. 7A illustrates a bottom perspective view of the electronics assembly of FIG. 6.
Figure 7B:
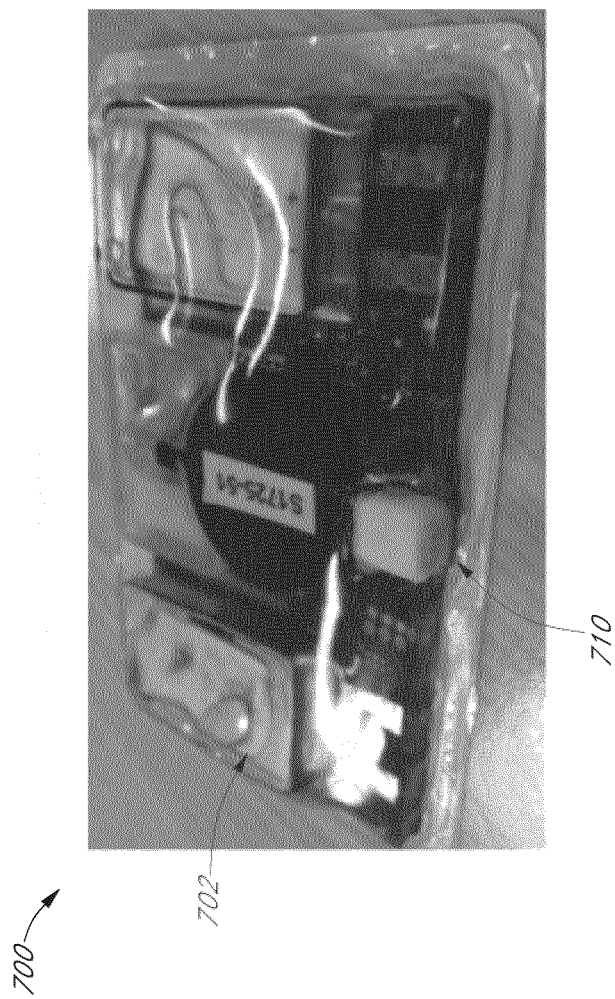
FIGS. 7B-7D show embodiments of a lower wound facing surface of an electronics assembly.
Figure 7C:
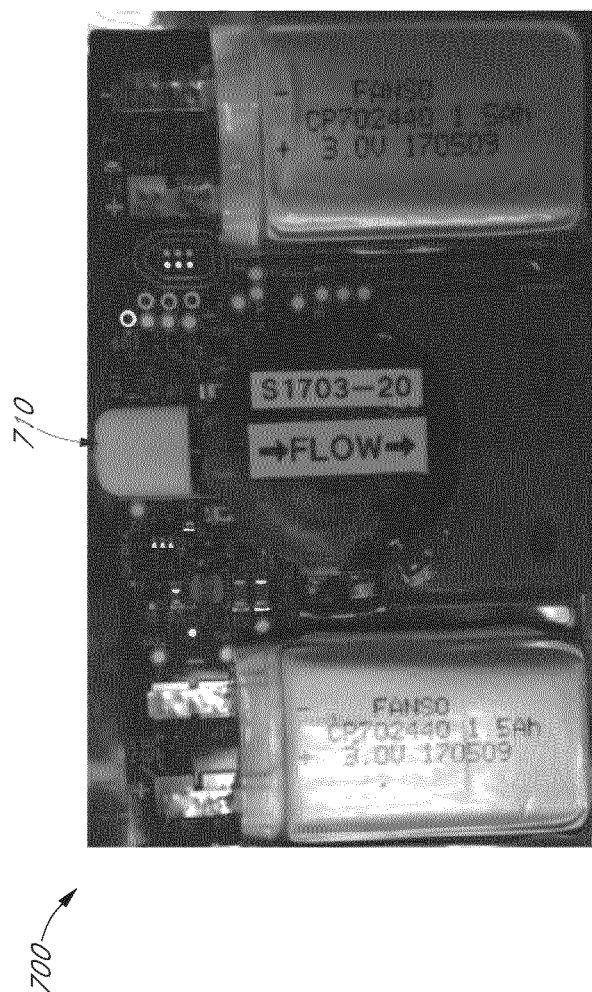
Figure 7D:
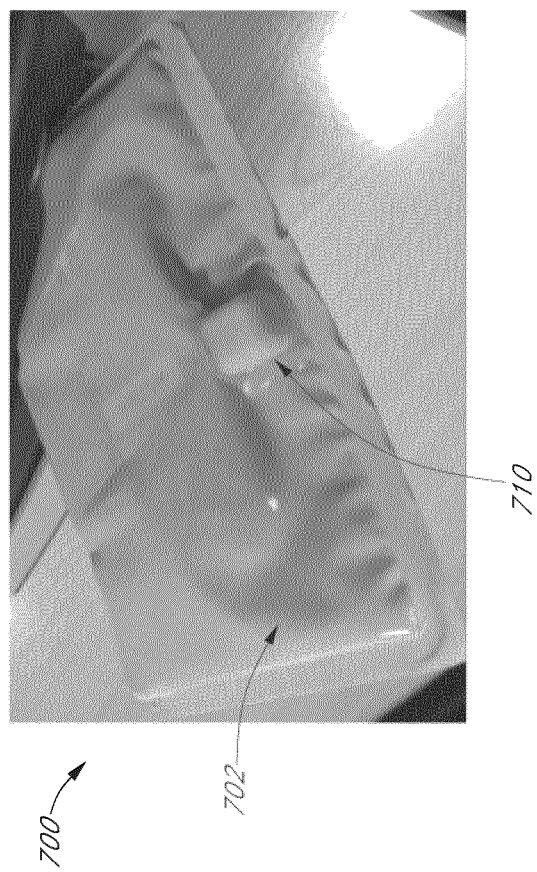
Figure 7E:
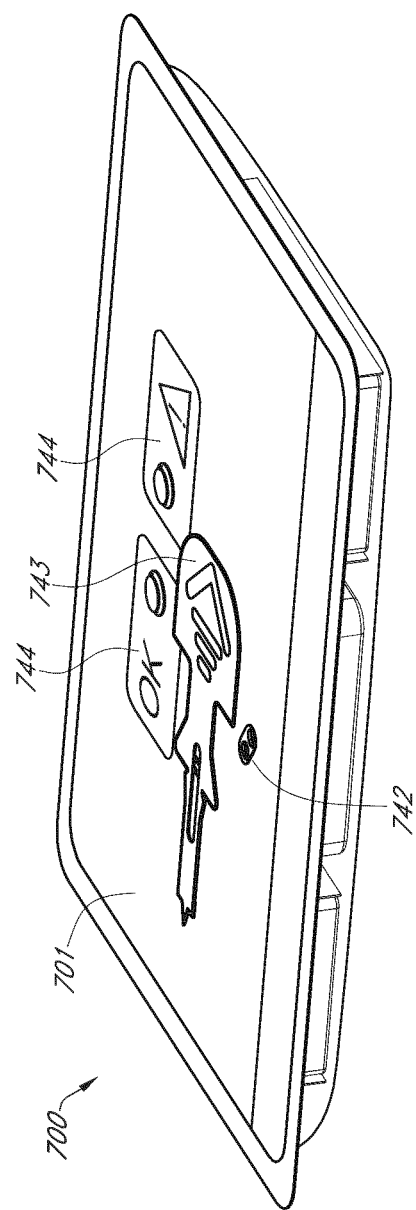
FIG. 7E illustrates a top perspective view of the electronics assembly of FIG. 6.
Figure 7F:
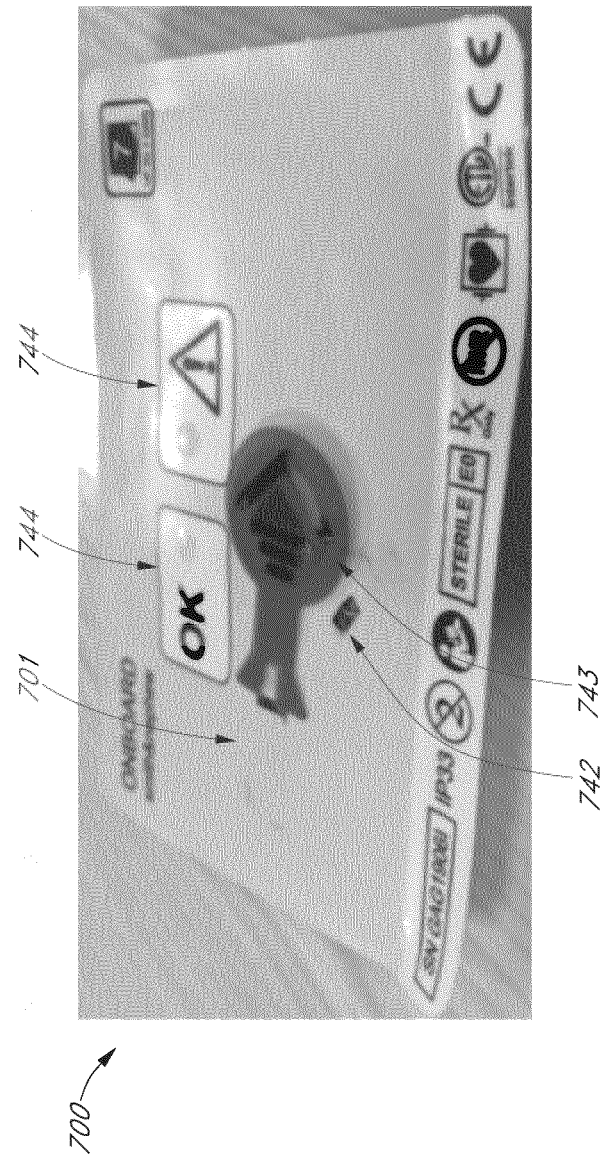
FIGS. 7F-7G show embodiments of an upper surface of an electronics assembly.
Figure 7G:
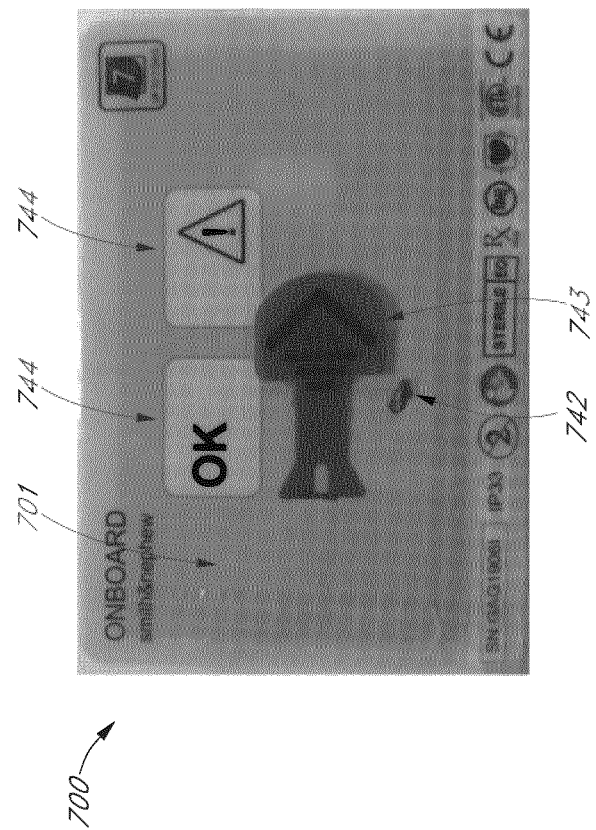

FIGS. 7E-7G show an upper surface of the plate 701 of the electronics assembly 700. The upper surface of the plate can include an on/off switch or button cover 743, indicator portions 744, and/or vent holes 742. The on/off switch cover or button 743, indicator portions 744, and/or vent holes 742 can be similar to the switch cover or button and indictor portions described with reference to FIGS. 3A-3C, 4A-4B, and 5A-5B.

In some embodiments, as shown in FIGS. 7E, 7F, and 7G, the switch or button cover 743 can be positioned over the switch on the flexible circuit board of the electronics components as described herein. In some embodiments, the plate can include embossed features for the switch cover 743. In some embodiments, the embossed features of the switch cover 743 can prevent accidental activation or deactivation of the device. In some embodiments, the switch or switch cover 743 can include a tab on the switch to prevent accidental activation or deactivation.

In some embodiments, as shown in FIGS. 7E, 7F, and 7G, the indicator portions can include visual symbols or words to indicate the condition of the wound dressing and electronics. For example, as shown in FIGS. 7E, 7F, and 7G, one indicator portion can read "OK". When the LED or light source associated with the "OK" indicator portion is illuminated the user is provided an indication that the dressing or electronics are functioning properly. An indicator portion can have a symbol, for example, a caution symbol similar to the symbol shown in FIG. 7E-7G. When the LED or light source associated with the caution symbol on the indicator portion is illuminated the user is provided an indication that the dressing or electronics may not be functioning properly and/or there may be a leak.

The vent holes 742 of the plate can allow exhaust from the pump outlet mechanism to pass through the plate and exit the wound dressing to be exhausted to the atmosphere.

Figure 7H:
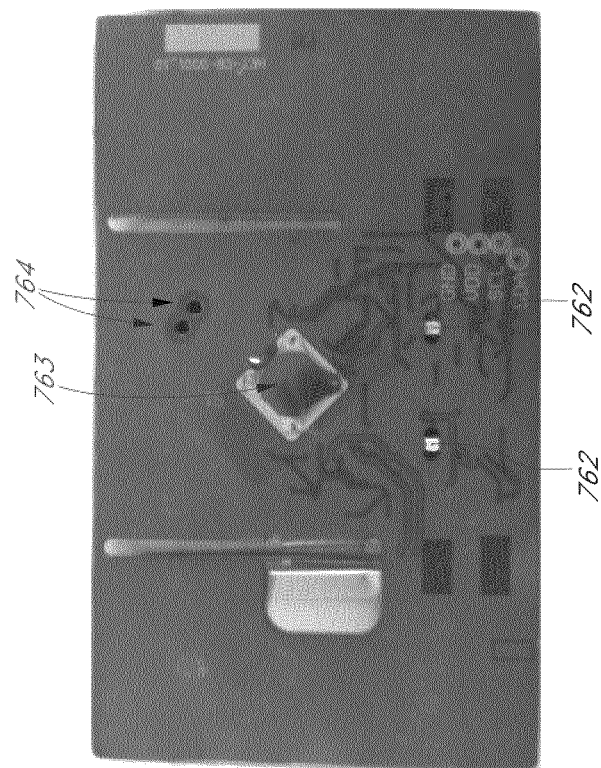
FIG. 7H illustrates an embodiment of a top surface of a flexible circuit board of the electronics unit.

FIG. 7H illustrates an embodiment of a top surface of a flexible circuit board of the electronics unit. The top surface of the flexible circuit board can include light or LED indicators 762, switch or button 763, and vent apertures 764 as illustrated in FIG. 7H and described in more detail herein.

Figure 7I:
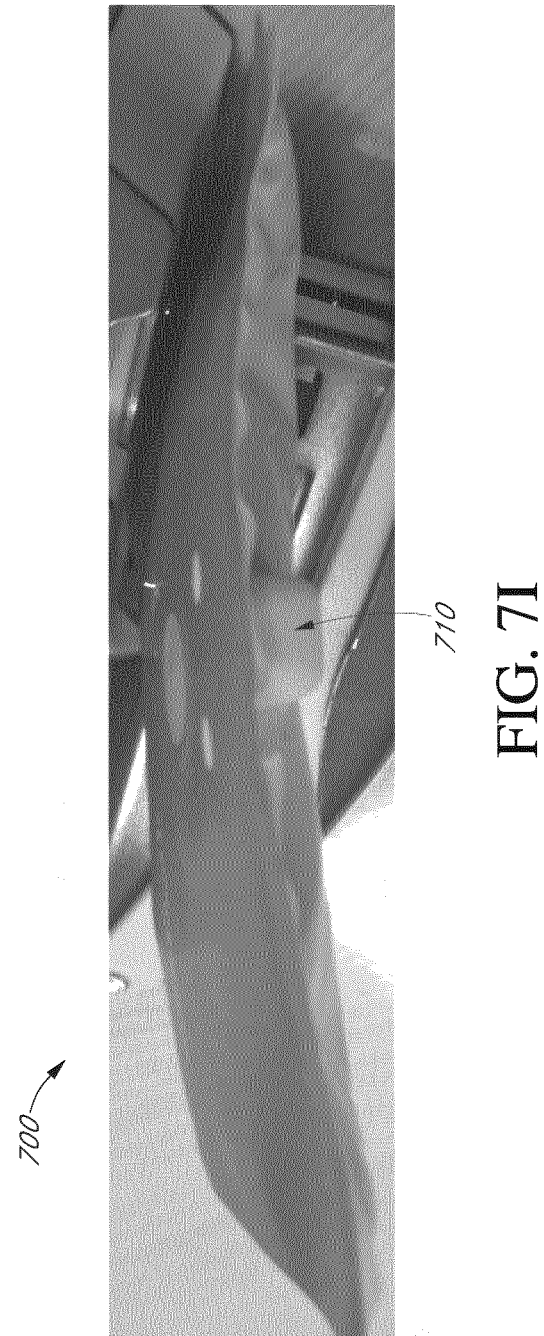
FIG. 7I illustrates a side view of an embodiment of an electronics assembly.

FIG. 7I illustrates a side view of an embodiment of the electronics assembly 700 and the pump inlet protection mechanism 710 is visible.

The electronics assembly 700 with the pump inlet protection mechanism 710 extending from and sealed to the film 702 can be positioned within the aperture 520 in the cover layer 513 and absorbent layer(s) (not shown) as shown in FIGS. 5A-5B and described in more detail herein. In some embodiments, the perimeter of the electronics assembly 700 can be sealed to a top surface of the outer perimeter of the aperture 520 in the cover layer 513 as shown in FIGS. 5A-5B and described in more detail with reference to FIGS. 9A-9B herein. In some embodiments, the electronics assembly 700 is sealed to the cover layer 513 with a sealant gasket, adhesive, heat welding, adhesive bonding, ultrasonic welding, RF welding, or any other attachment or bonding technique. In some embodiments, the electronics assembly 700 can be permanently sealed to the cover layer 513 and could not be removed from the cover layer without destroying the dressing.

In some embodiments, the electronics assembly 700 can be utilized in a single dressing and disposed of with the dressing. In other embodiments, the electronics assembly 700 can be utilized in a series of dressings.

Electronic Assembly Incorporated Within the Wound Dressing

Figure 8:
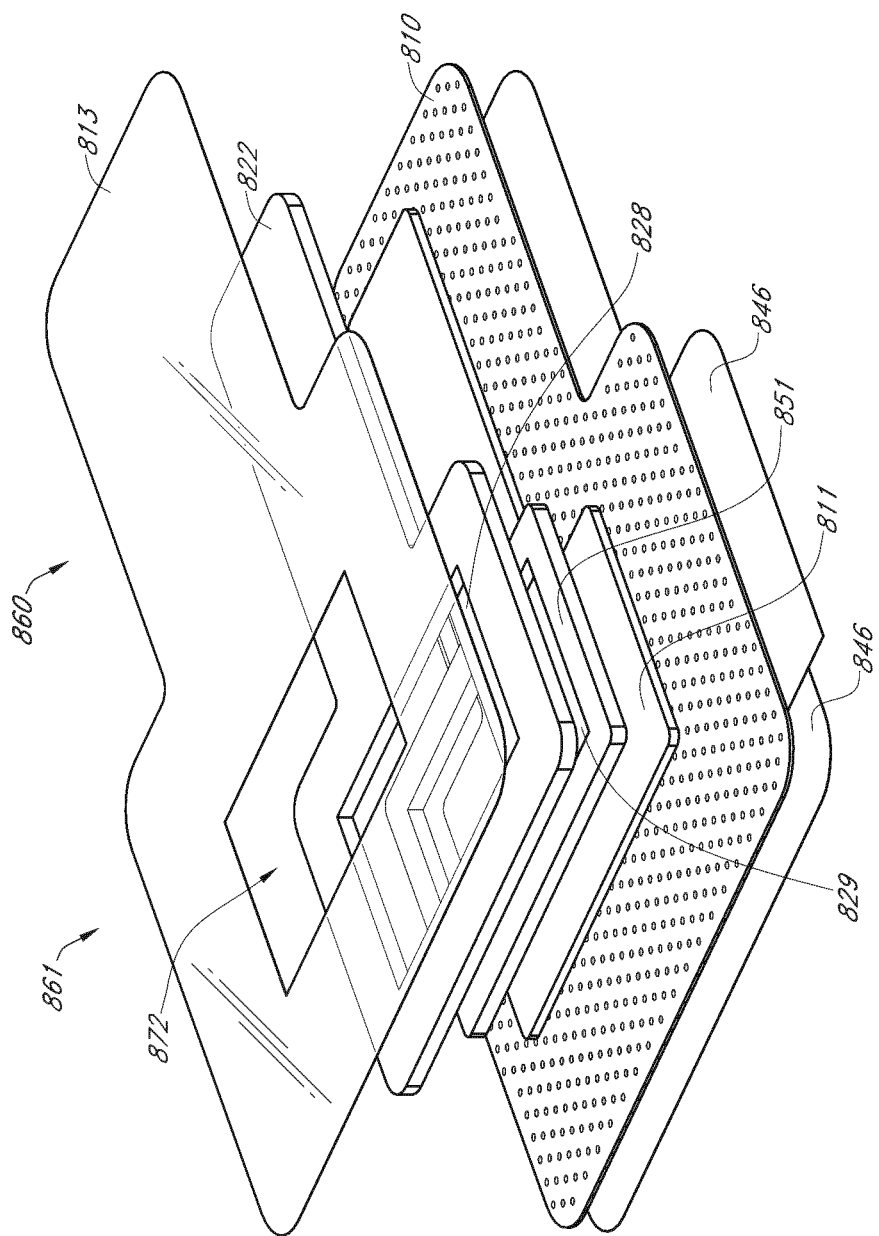
FIGS. 8 and 9A illustrate an embodiment of a wound dressing incorporating an electronics assembly within the wound dressing layers.

FIG. 8 illustrates an embodiment of wound dressing layers for a wound dressing that can be used with the incorporates electronics components and/or electronics assembly described herein. The dressing layers and components of FIG. 8 can be similar to the dressing layers and components described in FIG. 3A. However, the wound dressing illustrated in FIG. 8 can incorporate electronic components and negative pressure source enclosed within an electronics assembly similar to the electronics assembly 400, 500, 600, and 700 described with reference to FIGS. 4A-4B, FIGS. 5A-5B, FIG. 6, and FIGS. 7A-7I. FIG. 8 illustrates a wound dressing with a wound contact layer 810 configured to contact the wound. A transmission layer or spacer layer 811 is provided over the wound contact layer. The transmission layer 811 can assist in transmitting and distributing negative pressure over the wound site.

A first layer of apertured absorbent material 851 can be provided over the transmission layer 811. The first apertured absorbent layer 851 can include one or more apertures 829. In some embodiments, the aperture 829 can be sized and shaped to fit an electronics assembly and/or electronics unit therein. The first apertured absorbent layer 851 can be sized and shaped to the size of the electronics area 861 and does not extend into the absorbent area 860. In some embodiments, the aperture 829 can be shaped and sized to fit the electronics assembly formed from the plate and film described with reference to FIGS. 4A-7I.

A second apertured absorbent layer 822 can be provided over the first absorbent layer 851. In some embodiments, the second absorbent layer 822 includes one or more apertures 828. The second absorbent layer 822 can be sized and shaped to the size of the electronics area 861 and the absorbent area 860. In some embodiments, the aperture 828 can be shaped and sized to fit the electronics assembly formed from the plate and film described with reference to FIGS. 4A-7I.

A cover layer or backing layer 813 can be positioned over the absorbent material 822. The cover layer 813 can form a seal to the wound contact layer 810 at a perimeter region enclosing the absorbent layers 822 and 851 and the transmission layer 811. In some embodiments, the cover layer 813 can be a flexible sheet of material that forms and molds around the dressing components when they are applied to the wound. In other embodiments, the cover layer 813 can be a material that is preformed or premolded to fit around the dressing components as shown in FIG. 8. As used herein, the terms cover layer and backing layer can be used interchangeably to refer to the layer of material in the dressing configured to cover the layers of the wound dressing.

In some embodiments, the cover layer or backing layer 813 can include an aperture 872. The aperture 372 can be positioned over at least a portion of the aperture 828 in the absorbent layer 822 to allow access and fluid communication to at least a portion of the absorbent layers 822 and 851, transmission layer 811, and would contact layer 810 positioned below. The wound contact layer, the transmission layer, and/or the absorbent layer can be optional layers and the wound dressing can be formed without any of these layers.

An electronics assembly can be positioned in the apertures 828, 829, and 872 of the first and second absorbent material 851 and 822 and the cover layer 813. The electronics assembly can include a pump, power source, and a printed circuit board as described with reference to FIGS. 4A-5B, 6, and 7A-7I.

Before use, the dressing can include one or more delivery layers 846 adhered to the bottom surface of the wound contact layer. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Figure 9A:
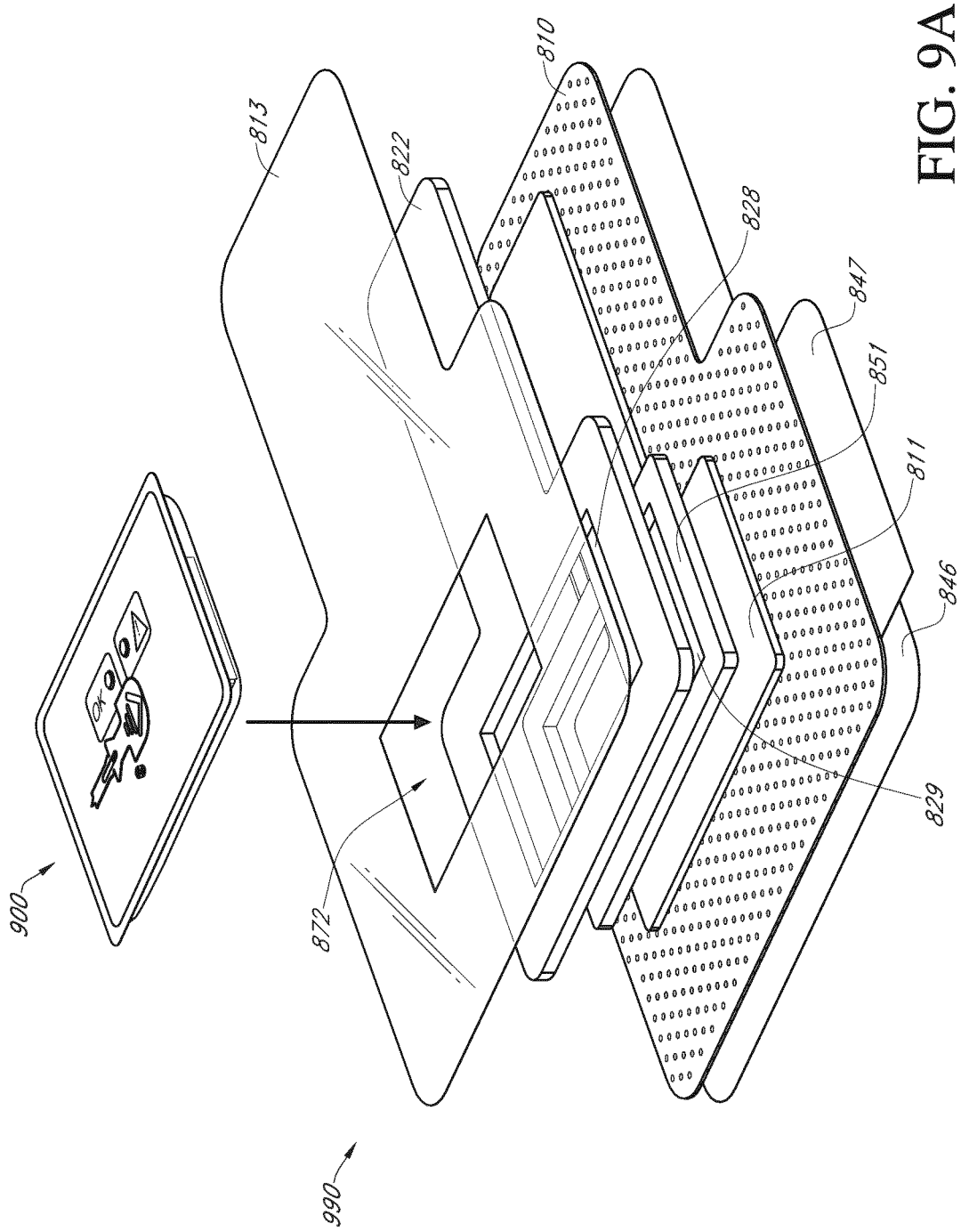

FIG. 9A illustrates an embodiment of a wound dressing incorporating an electronics assembly 900 within the wound dressing layers 990. The electronics assembly 900 can be provided within the aperture 872 in the cover layer and apertures 829 and 828 in the first and second absorbent layers. In some embodiments, the electronics assembly 900 can seal to the outer perimeter of the aperture 872 of the cover layer.

The electronics assembly 900 can include the pump inlet protection mechanism extending from and sealed to the film as described in FIGS. 6 and 7A-7I. The electronics assembly 900 can be positioned within the apertures 872, 829, 828 in the cover layer and absorbent layer(s) as shown in FIG. 9A. In some embodiments, the perimeter of the electronics assembly 900 can be sealed to a top surface of the outer perimeter of the aperture 872 in the cover layer as shown in FIG. 9A. In some embodiments, the electronics assembly 700 is sealed to the cover layer 813 with a sealant gasket, adhesive, heat welding, adhesive bonding, ultrasonic welding, RF welding, or any other attachment or bonding technique. In some embodiments, the electronics assembly 900 can be permanently sealed to the cover layer 813 and could not be removed from the cover layer without destroying the dressing.

In some embodiments, the electronics assembly 900 can be utilized in a single dressing and disposed of with the dressing. In other embodiments, the electronics assembly 900 can be utilized or re-used (e.g., after sterilization) in a series of dressings.

Figure 9B:
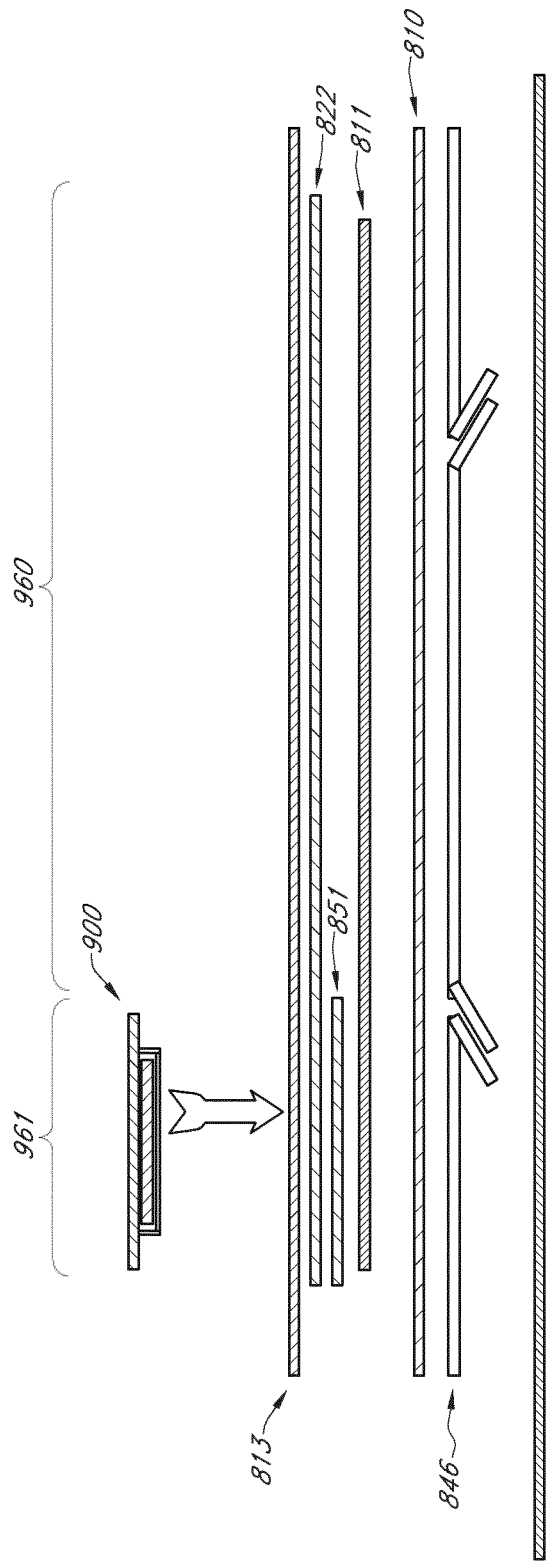
FIG. 9B illustrates a cross sectional layout of the material layers of the wound dressing incorporating an electronics assembly within the dressing.

FIG. 9B illustrates a cross sectional layout of the material layers of the wound dressing incorporating an electronics assembly within the dressing. The dressing included multiple material layers and an electronics assembly 900. The wound dressing can include an electronics area 961 including the electronics and an absorbent area or dressing area 960 that is intended to be applied to the wound as described with reference to FIGS. 1A-1C.

As described herein, the one or more material layers can extend into both the electronics area 961 and the dressing area 960. The dressing can include a wound contact layer 810, transmission layer 811, absorbent layers 822 and 851, and a cover or backing layer 813 as illustrated in FIG. 9B. The absorbent layers 822 and 851 and cover layer 813 can include recesses or cutouts to receive the components of the electronics assembly 900 as described with reference to FIG. 9A. In some embodiments, the small apertured absorbent layer 851 can be positioned on top of the large apertured absorbent layer 822. In other embodiments, as illustrated in FIGS. 9A-9B the small apertured absorbent layer 851 can be positioned below of the large apertured absorbent layer 922.

In some embodiments, the electronics assembly 900 can be inserted and affixed in the dressing layers. As illustrated in FIG. 9A, the lower wound facing face of the film enclosing the electronics assembly can be sealed directly to the upper surface of the cover layer 813 of the dressing.

Before use, the dressing can include a delivery layer 846 adhered to the bottom surface of the wound contact layer 810. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Pressure Indicators

Figure 10A:
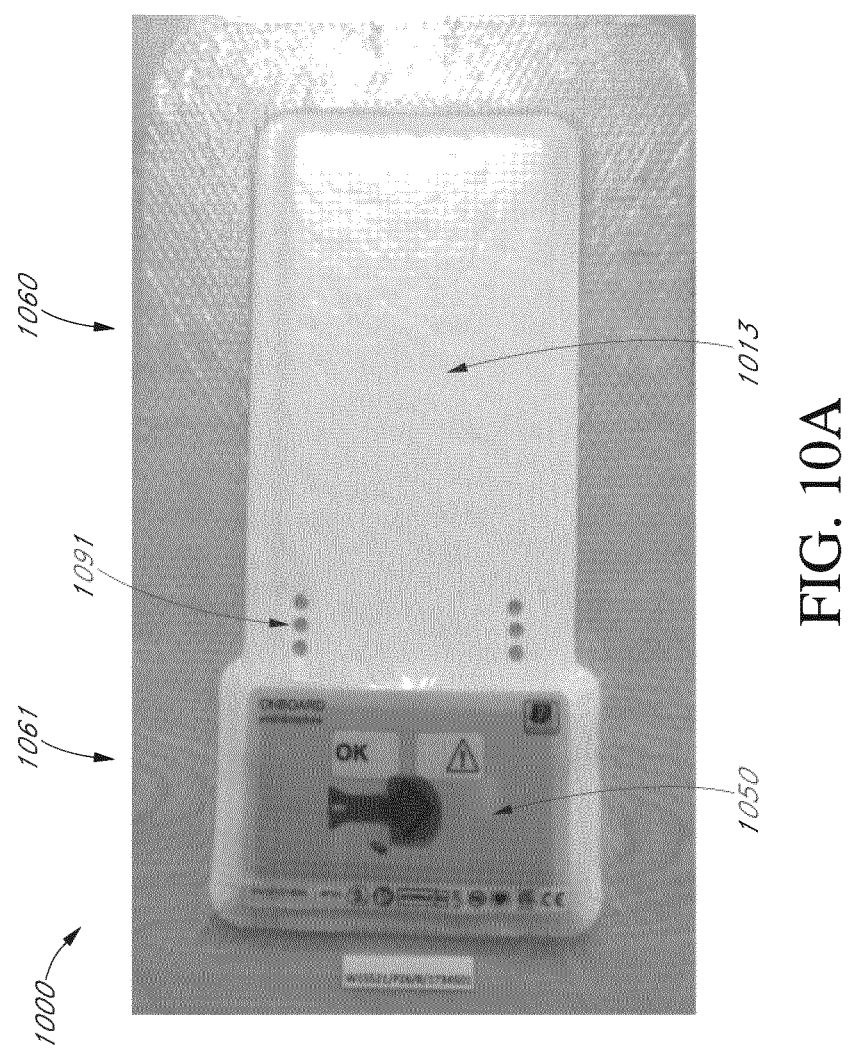

FIG. 10A illustrates a wound dressing embodiment incorporating an electronics assembly within the dressing layers. As illustrated in FIG. 10A, the wound dressing comprises an absorbent area 1060 and an electronics area 1061. The electronics assembly 1050 can be incorporated into the electronics area 1061 of the dressing. The outer perimeter of the electronics assembly 1050 can be sealed to the perimeter of the aperture (not shown) in the cover layer 1013 as described in more detail with reference to FIGS. 9A-9B.

FIG. 10A illustrates negative pressure indicators 1091 within the wound dressing to indicate when the components within the wound dressing 1000 are under negative pressure. As illustrated in FIG. 10A, the wound dressing includes an absorbent area 1060 adjacent to or offset from an electronics area 1061. In some embodiments, the absorbent area 1060 can include absorbent material to absorb and retain fluids and/or wound exudate from the wound. In some embodiments, the electronics area 1061 can include the electronics assembly and/or electronics components as described herein. The negative pressure indicator can be a mechanical indicator. In some embodiments, the negative pressure indicator can be an indicator that does not require direct line of sight from the patient. For example, the negative pressure indicator can be an indicator that can be touched or felt by a patient or user. The negative pressure indicator 1091 can be aperture(s) or cut out(s) in an absorbent material of the dressing. Once negative pressure is applied under the cover layer, the dressing will tighten and the cover layer will compress as it sucks down into the aperture(s) or cut out(s) in the absorbent material.

Figure 10B:
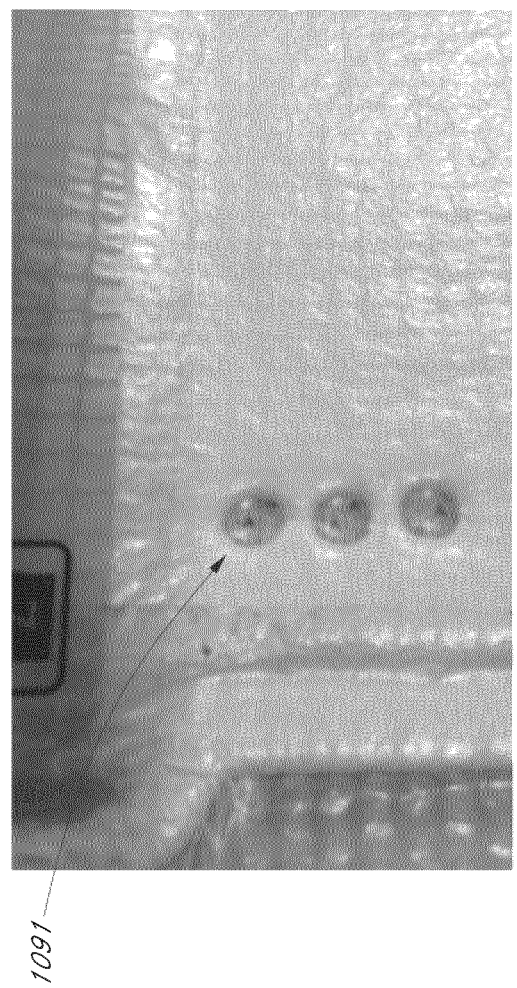

In some embodiments, the negative pressure indicators 1091 can be a small hole array as illustrated in FIG. 10A. In some embodiments, there can be three small holes in the absorbent area 1060 of the dressing. In some embodiments, two sets of three small hole arrays can be used on opposite sides of the dressing extending longitudinally along the side edges of the dressing as shown in FIG. 10A. In some embodiments, an individual negative pressure indicator can be about 4 mm to about 5 mm in diameter. FIG. 10A illustrates the negative pressure indicators 1091 in the decompressed position where the indicators feel and look soft. FIG. 10B illustrates the negative pressure indicators 1091 in the compressed position where the indicators feel and look tight.

The negative pressure indicators can be formed from different types of step changes or indentations created in the dressing as a result of a cut out or hole in the absorbent layer. In some embodiments, the negative pressure indicator can be formed from the hole or cut out in the absorbent material with the cover layer covering the hole or cut out. In some embodiments, the hole or cut out in the absorbent material can be circular, rectangular, triangular, oval, or any other shape. When no vacuum is applied the area would feel loose, whilst under negative pressure the area would tighten and the stepped topography or indentation in the cover layer would be apparent. The stepped topography can be visualized and/or felt by the user. A small hole in the absorbent material as illustrated in FIGS. 10A-10B can be used. In other embodiments, a large hole in the absorbent material coupled with another film material or a rectangular strip in the absorbent material coupled with another film material can be used.

The small hole cut in the absorbent material can be used in combination with the adhesive coated top film. The interaction between the two behave as described previously. Under pressure the absorbent material compresses and the film tightens revealing a film covered hole. This hole can be felt when the system is under negative pressure. When the system returns to ambient pressure, the film "relaxes" or "springs" back to its original state and the hole cannot be as easily felt through the top film material. FIGS. 10C-10D illustrate cross sectional views of the holes before (FIG. 10C) and during (FIG. 10D) negative pressure application. The small hole (about 4 mm to about 5 mm in diameter) negative pressure indicators can allow for a tight step change topography when negative pressure is applied whilst hiding the stepped hole area when the dressing is returned to ambient pressure.

In other embodiments, a large hole with a non-adhesive film can be used as a negative pressure indicator. The large hole can be an aperture or cut out as described with the small holes. However, since the cover layer can be coated with an adhesive material, a non-adhesive film 1092 can be used within the large hole in the absorbent material 1022 to prevent the cover layer 1013 from remaining fixed to the lower layers of the dressing after the cover layer 1013 has been compressed down into the large hole and then returned to ambient pressure.

Figure 10E:
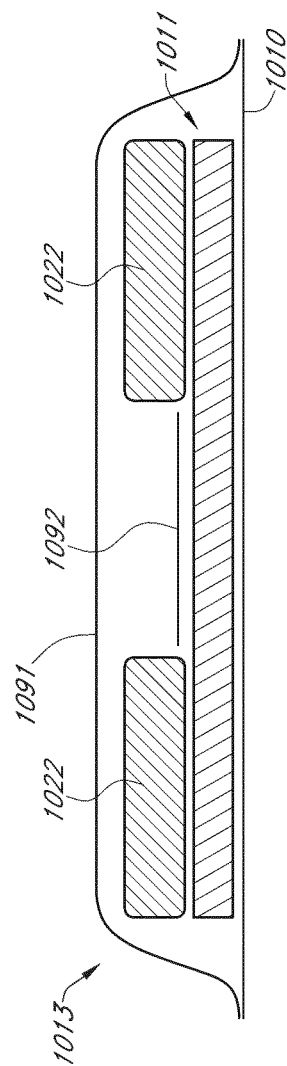

FIG. 10E illustrates a cross sectional view of an embodiment of a wound dressing with a negative pressure indicator 1091 with a large hole aperture in the absorbent material 1022. As illustrated in FIG. 10E, the non-adhesive film 1092 can be positioned within the aperture or cut out in the absorbent material 1022. When the system is under negative pressure, the cover layer 1013 can stick to the non-adhesive film material 1092 and tighten around the absorbent material 1022 creating the step change topography in the dressing defining the negative pressure indicator 1091. Once the dressing returns to ambient pressure, the cover layer 1013 relaxes back to its original state. In some embodiments, the large hole can be a circular hole of 12 mm (about 12 mm) in diameter. In some embodiments, more than one large hole can be used. In some embodiments, an array of large holes can be used.

Additionally, in another embodiment, a strip within the absorbent material can be used with a non-adhesive film. This embodiment can be similar to the method as outline with the large hole and film described previously. However, instead of a large hole within the absorbent material, there can be a strip extending along at least a portion of the length or width of the absorbent material. In some embodiments, when the dressing has a 'T' shape, the strip could be used to separate the electronics area from the absorbent area while still retaining both parts within the same dressing profile. In some embodiments, similar to the use in the large hole, the non-adhesive film can be cut to the size of the strip and used in the strip recess in the absorbent material as to prevent the top film from sticking to the lower spacer layer when the cover layer is compressed.

Figure 10F:
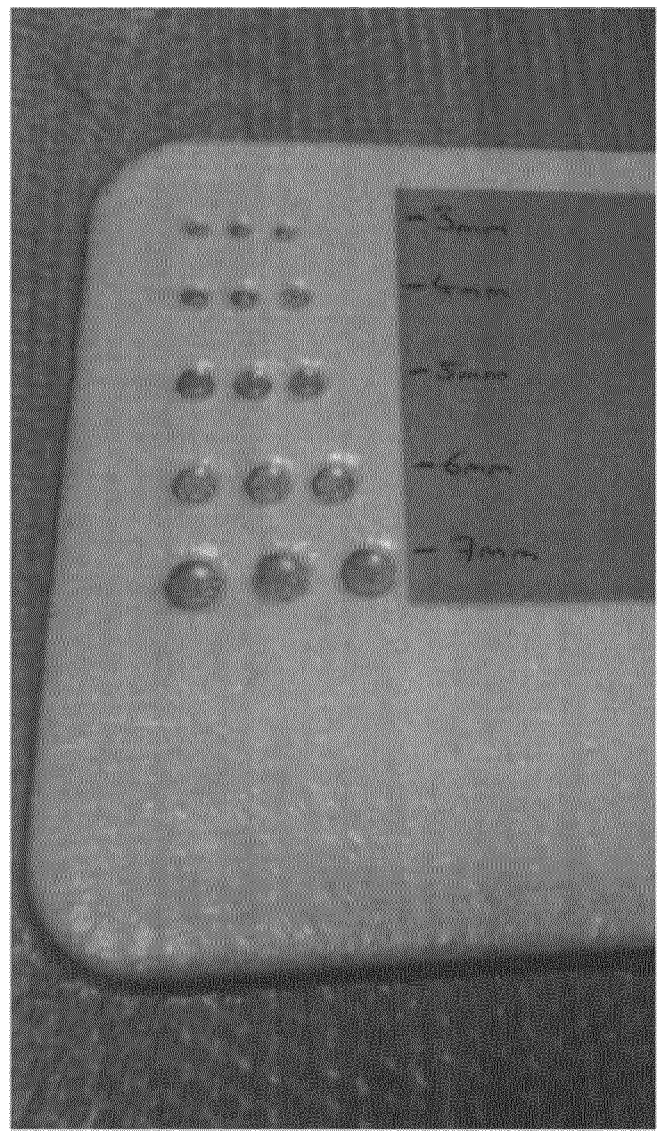
Figure 10G:
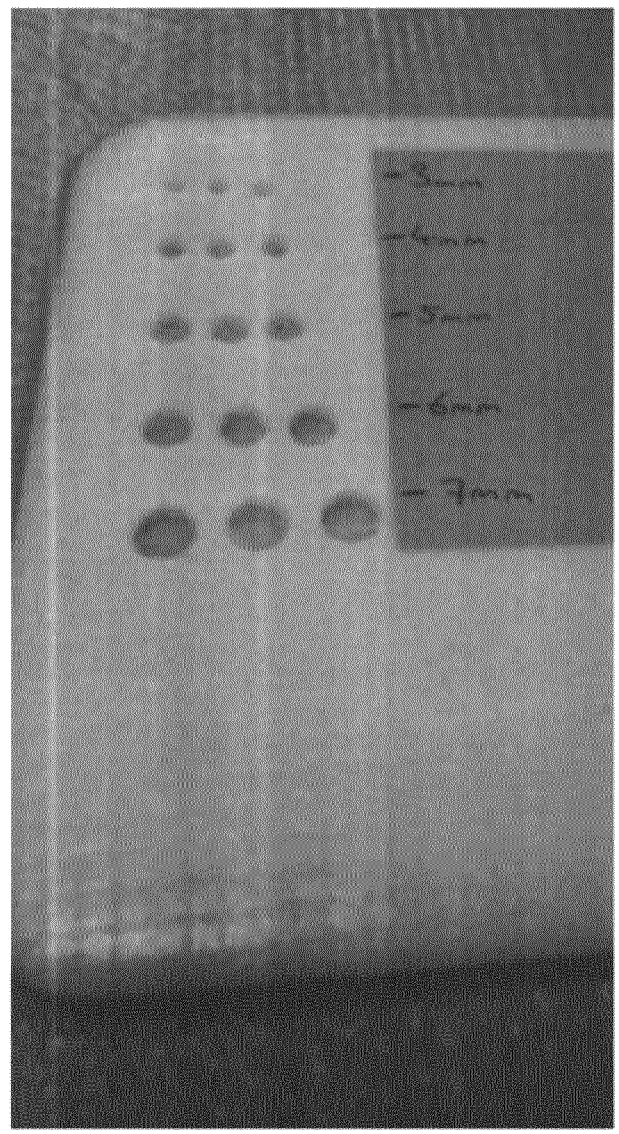

FIGS. 10F-10G illustrate a variety of holes in 5 rows of 3 hole arrays cut in the absorbent material, each row increasing in size from 3 mm to 7 mm diameters. The 3 hole arrays illustrate the various hole sizes that can be used in a wound dressing.

In some embodiments, the holes can be less than 3 mm, 3 mm (about 3 mm), 4 mm (about 4 mm), 5 mm (about 5 mm), 6 mm (about 6 mm), 7 mm (about 7 mm), or greater than 7 mm in diameter. FIG. 10F illustrates the array of holes with various diameter holes under negative pressure. FIG. 10G illustrates the array of holes with various diameter holes under ambient pressure.

FIGS. 11A-11D, 12A-12G, and 13A-13B illustrate embodiments of a wound dressing incorporating an electronics assembly and negative pressure indicators within the dressing layers.

Figure 11A:
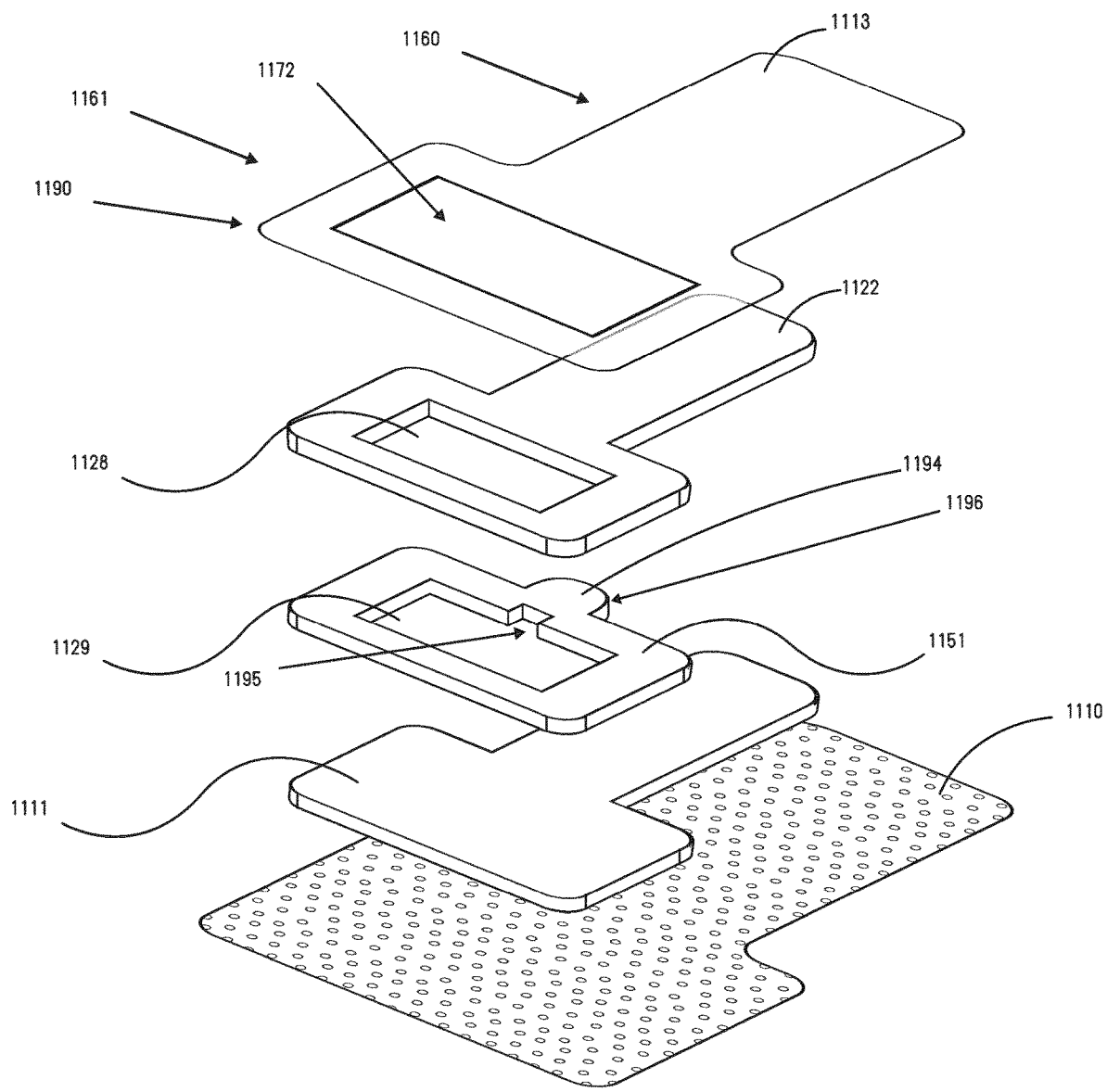
FIGS. 11A-11B illustrates an embodiment of a wound dressing incorporating an electronics assembly and negative pressure indicators within the dressing layers.

FIG. 11A illustrates an embodiment of wound dressing layers for a wound dressing that can incorporate electronic components and/or an electronics assembly described herein. The dressing layers and components of FIG. 11A can be similar to the dressing layers and components described in FIGS. 3A, 8, and 9A-9B. However, the wound dressing illustrated in FIG. 11A can incorporate electronic components and negative pressure source enclosed within an electronics assembly similar to the electronics assembly 400, 500, 600, and 700 described with reference to FIGS. 4A-4B, FIGS. 5A-5B, FIG. 6, FIGS. 7A-7I, 8, and 9A-9B. FIG. 11A illustrates a wound dressing with a wound contact layer 1110 configured to contact the wound. A transmission layer or spacer layer 1111 is provided over the wound contact layer. The transmission layer 1111 can assist in transmitting and distributing negative pressure over the wound site.

A small, apertured absorbent layer 1151 can be provided over the transmission layer 1111. In some embodiments, the small absorbent layer 1151 includes one or more apertures 1129. The small apertured absorbent layer 1151 can be sized and shaped to the size of the electronics area 1161. In some embodiments, the aperture 1129 can be shaped and sized to fit the electronics assembly formed from the plate and film described with reference to FIGS. 4A-7I.

A large, apertured absorbent material 1122 can be provided over the small apertured absorbent layer 1151. The large apertured absorbent layer 1122 can include one or more apertures 1128. In some embodiments, the aperture 1128 can be sized and shaped to fit an electronics assembly and/or electronics unit therein. The large absorbent layer 1122 can be sized and shaped to the size of the electronics area 1161 and the absorbent area 1160.

In some embodiments, the large, apertured absorbent layer and the small, apertured absorbent layer can be formed as one layer of absorbent material with varying thickness. For example, the single absorbent layer can have a portion of the absorbent layer in the electronics area that is thicker than a portion of the absorbent layer in the absorbent area.

A cover layer or backing layer 1113 can be positioned over the absorbent layers 1151 and 1122. The cover layer 1113 can form a seal to the wound contact layer 1110 at a perimeter region enclosing the absorbent layers 1122 and 1151 and the transmission layer 1111. In some embodiments, the cover layer 1113 can be a flexible sheet of material that forms and molds around the dressing components when they are applied to the wound. In other embodiments, the cover layer 1113 can be a material that is preformed or premolded to fit around the dressing components.

In some embodiments, the cover layer or backing layer 1113 can include an aperture 1172. The aperture 1172 can be positioned over at least a portion of the aperture 1128 in the absorbent layer 1122 to allow access and fluid communication to at least a portion of the absorbent layers 1122 and 1151, transmission layer 1111, and wound contact layer 1110 positioned below. The wound contact layer, the transmission layer, and/or the absorbent layer can be optional layers and the wound dressing can be formed without any of these layers.

FIG. 11A illustrates an embodiment of a wound dressing for incorporating an electronics assembly within the wound dressing layers 1190. The electronics assembly can be provided within the aperture 1172 in the cover layer and apertures 1129 and 1128 in the absorbent layers. In some embodiments, the electronics assembly 900 can seal to the outer perimeter of the aperture 1172 of the cover layer.

Figure 11B:
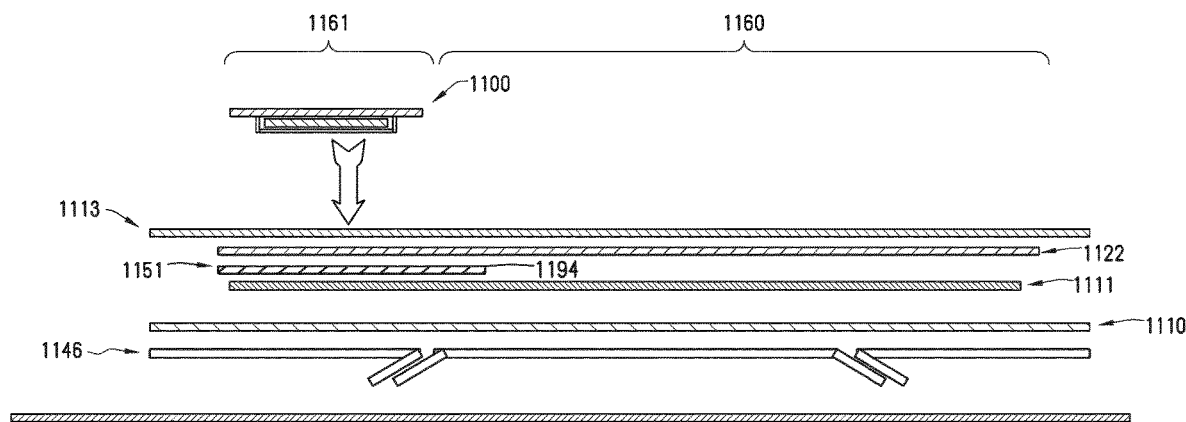

FIG. 11B illustrates a cross sectional layout of the material layers of the wound dressing incorporating an electronics assembly within the dressing. The dressing includes multiple material layers and an electronics assembly 1100. The wound dressing can include an electronics area 1161 including the electronics and an absorbent area or dressing area 1160 that is intended to be applied to the wound as described with reference to FIGS. 1A-1C.

As described herein, the one or more material layers can extend into both the electronics area 1161 and the dressing area 1160. The dressing can include a wound contact layer 1110, transmission layer 1111, a large absorbent layer 1122, a small absorbent layer 1151, and a cover or backing layer 1113 as illustrated in FIG. 11B. The absorbent layers 1122 and 1151 and cover layer 1113 can include recesses or cutouts to receive the components of the electronics assembly 1100 as described with reference to FIG. 11A. The recesses or cutouts in the absorbent layers 1122 and 1151 and cover layer 1113 are not shown in FIG. 11B as the cross section of the dressing shown in FIG. 11B is the portion of the wound dressing adjacent to or offset from the apertures or recesses. In some embodiments, the small absorbent layer 1151 can be positioned on top of the large absorbent layer 1122. In other embodiments, as illustrated in FIGS. 11A-11B, the small absorbent layer 1151 can be positioned below the large absorbent layer 1122.

In some embodiments, the electronics assembly 1100 can be inserted and affixed in the dressing layers. As illustrated in FIG. 11B, the lower wound facing face of the electronics assembly can be sealed directly to the upper surface of the cover layer 1113 of the dressing. Before use, the dressing can include a delivery layer 1146 adhered to the bottom surface of the wound contact layer 1110 as described herein.

As illustrated in FIGS. 11A-11D, an absorbent layer 1151 can include an extension 1194 formed from an extended area of material of the small apertured absorbent material. The extension 1194 of absorbent material of the absorbent layer 1151 can form a pressure indicator used to indicate the application of negative pressure to the wound dressing.

The absorbent layer 1151 can be sized and shaped to the size of the electronics area 1161 of the dressing and the extension 1194 extends into the absorbent area 1160 of the dressing as illustrated in FIGS. 11A-11B. As illustrated in FIGS. 11A-11D, the extension 1194 can extend from the portion 1195 of the absorbent layer 1151 that is in contact with or adjacent to a side of the electronics assembly 900 including the pump inlet mechanism when the dressing is assembled.

The absorbent layer 1151 can be shaped in order to form the extension 1194 that can be used as a pressure indicator when the device has reached negative pressure. When the dressing is not under negative pressure, the extension 1194 may not be visible or detectable, or may be less visible or detectable, from the surface of the dressing. In some embodiments, the extension 1194 may be visible but not apparent to the touch from the surface of the dressing. In some embodiments, the large absorbent material 1122 positioned above the small absorbent layer 1151 can help obscure the extension 1194 from view prior to the application of negative pressure. When negative pressure is applied to the dressing and the dressing layers are compressed under the force of the vacuum, the additional material of the extension 1194 can protrude from the upper or top surface of the dressing indicating that negative pressure has been applied. When negative pressure is applied to the dressing the extension 1194 can protrude upward from the upper surface of the dressing relative to the surrounding surface forming a visual and/or tactile protrusion. The protrusion of the extension 1194 relative to the surrounding upper surface of the dressing becomes more apparent and pronounced as negative pressure is applied to the dressing.

In some embodiments, the layer 1151 and/or extension 1194 can be any dressing material. For example, the layer 1151 and extension 1194 can be a transmission layer or an absorbent layer as described herein. In some embodiments, the layer 1151 and extension 1194 can be any non-woven material, woven material, foam material, and/or any other transmissive material to allow fluid communication between the pump inlet protection mechanism and the dressing layers.

In some embodiments, the pressure indicator can be an indicator material layer that is a layer of dressing material separate from any dressing layer. The indicator material layer can be any dressing material that is part of the laminated structure of the absorbent area and when negative pressure is applied to the dressing the indicator material layer can protrude upward from the upper surface of the dressing relative to the surrounding surface forming a visual and/or tactile protrusion. In some embodiments, the extension 1194 can be an indicator material layer that is attached to a dressing layer (i.e. the small absorbent layer) and can be used for an indication of the application of negative pressure to the dressing. In some embodiments, the indicator material layer can be a free floating piece of dressing material that is not connected to any other dressing layer. The free floating indicator material layer can be formed from any material that does or does not allow the transmission of fluid through the layer.

The extension 1194 can allow for both visual and tactile feedback for the user. The visual and tactile feedback can allow the user to identify if therapy has been carried out or not. By extending or shaping the absorbent layer 1151 in a way to provide the extension 1194, it can provide a visual indication when the dressing has reached negative pressure but also will allow for tactile feedback on whether or not the dressing is at negative pressure. A user can feel the additional layer of material from the extension 1194 in the absorbent area of the dressing when the layers are sucked down when negative pressure is applied. For example, when the wound dressing is positioned on an area of the body where the visual indicators cannot be observed by the user (i.e. the back of a patient), the protrusion of the material of the extension can be used to allow indication of the application of negative pressure and functioning of the dressing. The extension can maintain shape and rigidity under the application of negative pressure and will not become distorted.

Figure 11C:
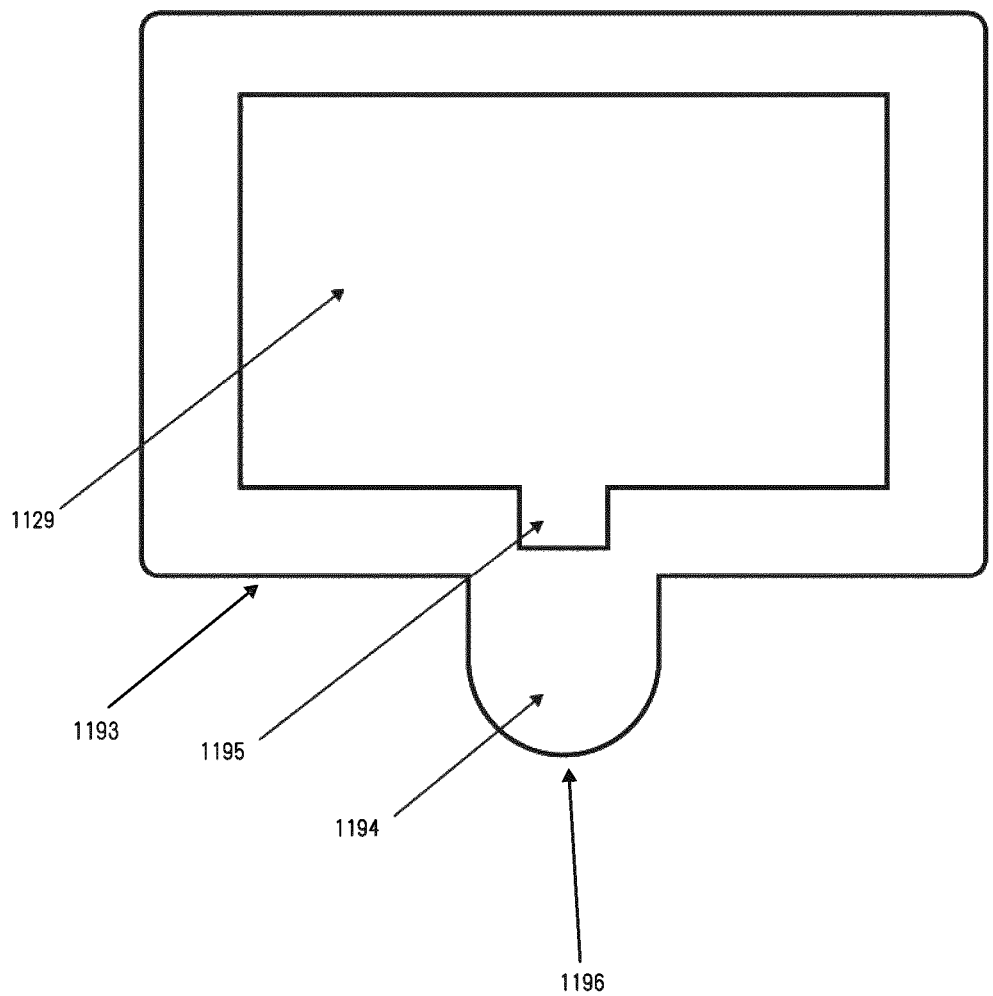
FIGS. 11C-11D illustrates an embodiment of a dressing layer of a wound dressing.
Figure 11D:
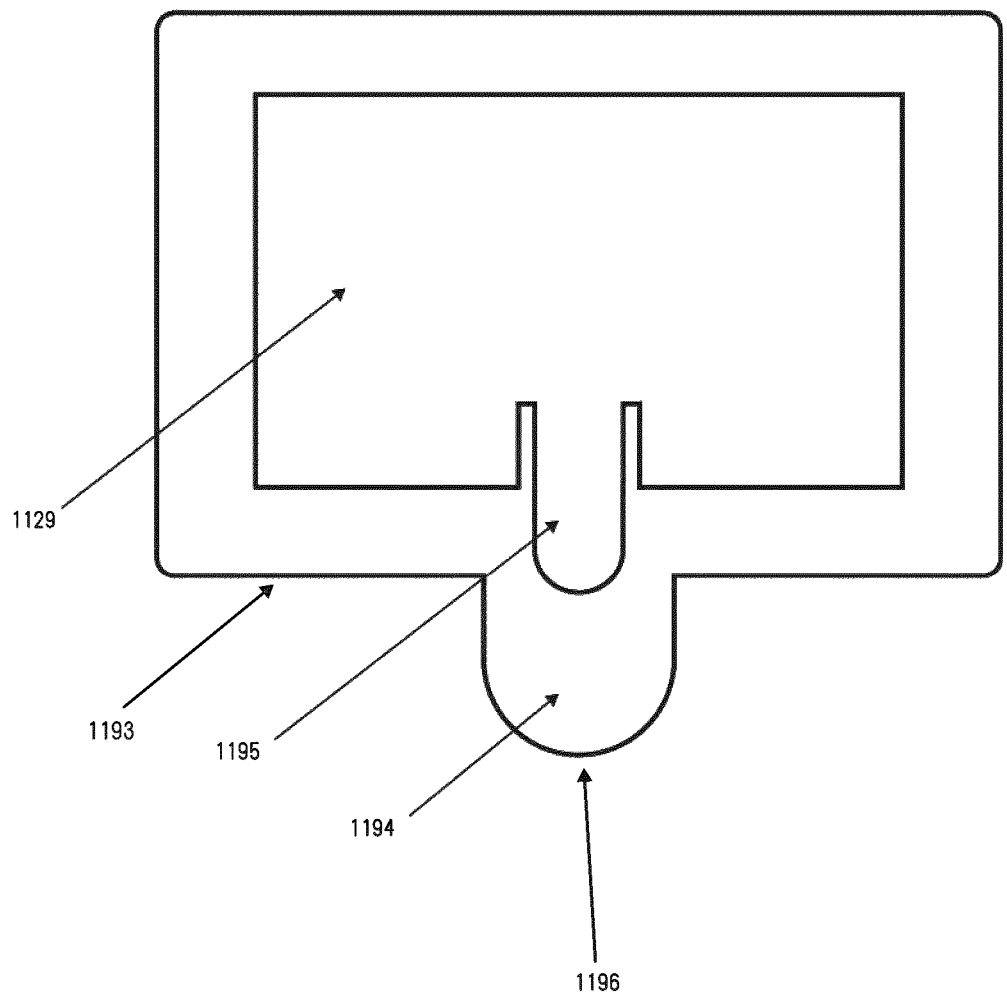

FIGS. 11C-11D illustrate a top view of the absorbent layer 1151 with an extension 1194. The absorbent layer 1151 can include aperture 1129 that is sized and shaped to fit an electronics unit therein. In some embodiments, the aperture 1129 can be shaped and sized to fit the individual components of the electronics unit (as described with reference to FIG. 3A) or can be sized and shaped to fit an electronics assembly (as described with reference to FIGS. 8, 9A-9B, and 11A-11B).

The absorbent layer 1151 can be sized and shaped to the size of the electronics area 1161 of the dressing, however, the extension 1194 can extend into the absorbent area 1160 of the dressing as illustrated in FIGS. 11A-11B, 12A-12G and 13A-13B.

As illustrated in FIGS. 11C-11D, the extension 1194 can be a semi-circle on a rectangle shape. In some embodiments, the extension 1194 can be a rectangle, semi-circle on a rectangle, a triangle, semi-circle, a rectangle, or any other shape. In some embodiments, the extension 1194 can be smaller than the cover layer. In some embodiments, the extension 1194 can be smaller than the absorbent area of the dressing. In some embodiments, the extension 1194 can be smaller than the absorbent material in absorbent area. The extensions can have a length that is parallel to the longitudinal axis of the dressing. The length of the extension can be measured from an edge 1193 of the absorbent layer 1151 to the furthest edge 1196 of the extension 1194. The extensions can have a length of 25 mm to 30 mm. In some embodiments, the extension 1194 can be any size and can extend the entire length of the absorbent area 1160 of the dressing. In some embodiments, the extension 1194 can have a length that is less than the length of the cover layer. In some embodiments, the extension 1194 can have a length that is less than the length of the absorbent area of the dressing. In some embodiments, the extension 1194 can have a length that is less than the length of the absorbent material in the absorbent area. The extension 1194 can be any length and extend any distance into the absorbent area as long as there are remaining surrounding areas in the absorbent area to allow the varying thickness of the absorbent area to be detectable. The shape and size of the extension 1194 can be large enough to act as a good tactile indicator as well as acting as a good visual indicator.

The wound dressing as described herein can have a longitudinal length that is parallel to a longitudinal axis that extends the length of the dressing passing through the electronics area 1161 and absorbent area 1160. The extension 1194 as illustrated in 11A-11D, 12A-12G, and 13A-13B can have a width that is perpendicular to the longitudinal axis of the dressing. In some embodiments, the extension 1194 can be 10 mm to 60 mm (about 10 mm to about 60 mm) wide at the largest width of the shape. In some embodiments, the extension 1194 can be about 25 mm wide at the largest width of the shape. In some embodiments, the extension 1194 can have a width that is less than the width of the cover layer. In some embodiments, the extension 1194 can have a width that is less than the width of the absorbent area of the dressing. In some embodiments, the extension 1194 can have a width that is less than the width of the absorbent material in absorbent area. In some embodiments, the extension can be any width. In some embodiments, the extension 1194 can extend the entire width of the absorbent area as long as there are remaining surrounding areas in the absorbent area to allow the varying thickness of the absorbent area to be detectable.

FIG. 11D illustrates a top view of an embodiment of the absorbent layer 1151 with an extension 1194. The absorbent layer 1151 of FIG. 11D is similar to the absorbent layer 1151 of FIG. 11C but the portion 1195 of the absorbent layer 1151 in FIG. 11D is shaped to provide more area between the pump inlet mechanism of the electronics assembly and the absorbent layer 1151 and extension 1194. The increased area between the pump inlet mechanism and the absorbent layer 1151 and extension 1194 can reduce the chance of the super absorbent material gelling in front of or adjacent to the pump inlet mechanism while providing the shaped extension 1194 to be implemented as a pressure indicator.

In some embodiments, the shape of the extension 1194 can be interconnected or transposed to allow for ease of cutting and manufacturing of the layer. For example, the shape of the extension can be a rectangle, semi-circle on a rectangle, semi-circle, or a rectangle. In some embodiments, the depth that the extension 1194 can protrude into the dressing can be between 5 mm to 45 mm (about 5 mm to 45 mm). In some embodiments, the depth that the extension 1194 can protrude into the dressing can be between 10 mm to 35 mm (about 10 mm to about 35 mm). In some embodiments, the extension 1194 can have any depth as long as there are remaining surrounding areas in the absorbent area to allow the varying thickness of the absorbent area to be detectable. In some embodiments, the semi-circle on a rectangle can allow the shape to protrude more into the dressing.

FIGS. 12A-12G illustrate the absorbent layer (not shown but similar to absorbent layer 1151 described in FIGS. 11C-11D) with extension 1294 incorporated into a wound dressing 1200. The wound dressing 1200 also includes a cover layer 1213, second absorbent layer 1222, and label 1241 as illustrated in FIGS. 12A-12G. The cover layer 1213 and second absorbent layer 1222 can be similar to the absorbent layer 1122 and cover layer 1113 described with reference to FIGS. 11A-11B.

Figure 12A:
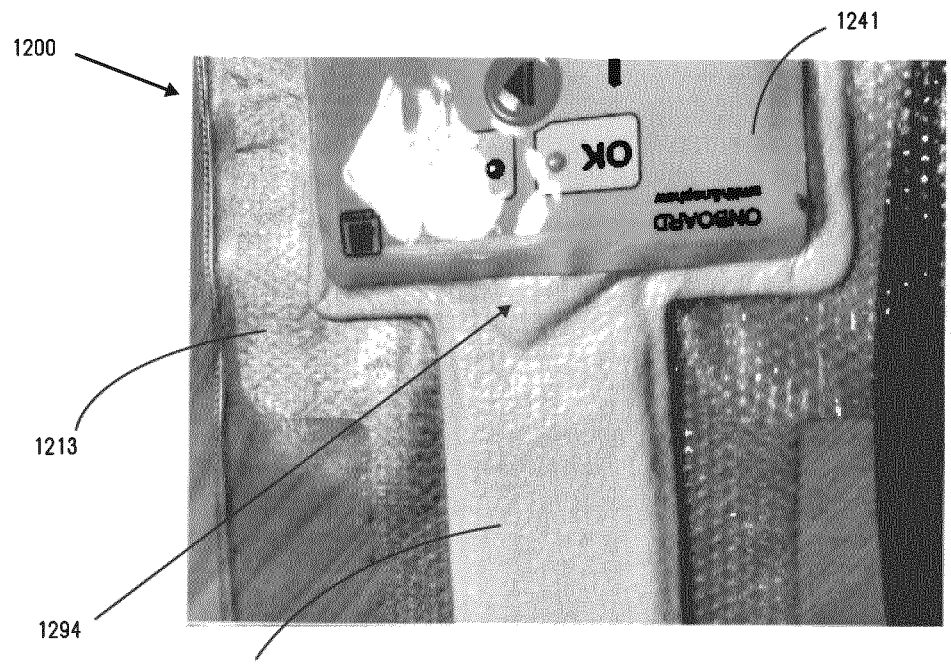
FIGS. 12A-12G, and 13A-13D illustrate embodiments of a wound dressing incorporating an electronics assembly and negative pressure indicators within the dressing layers.
Figure 12B:
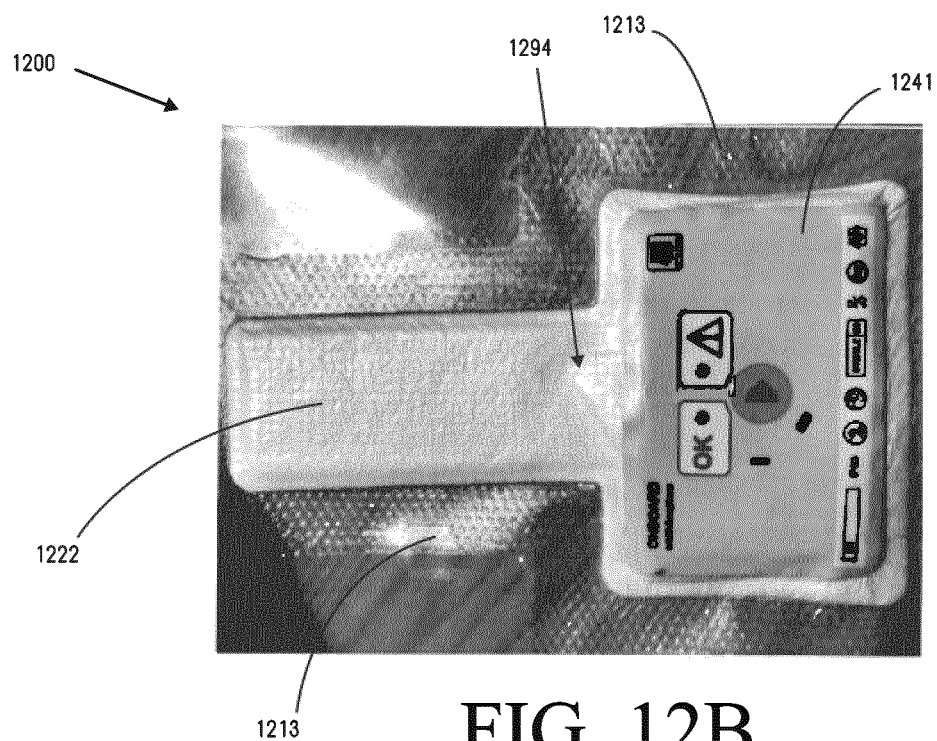
Figure 12C:
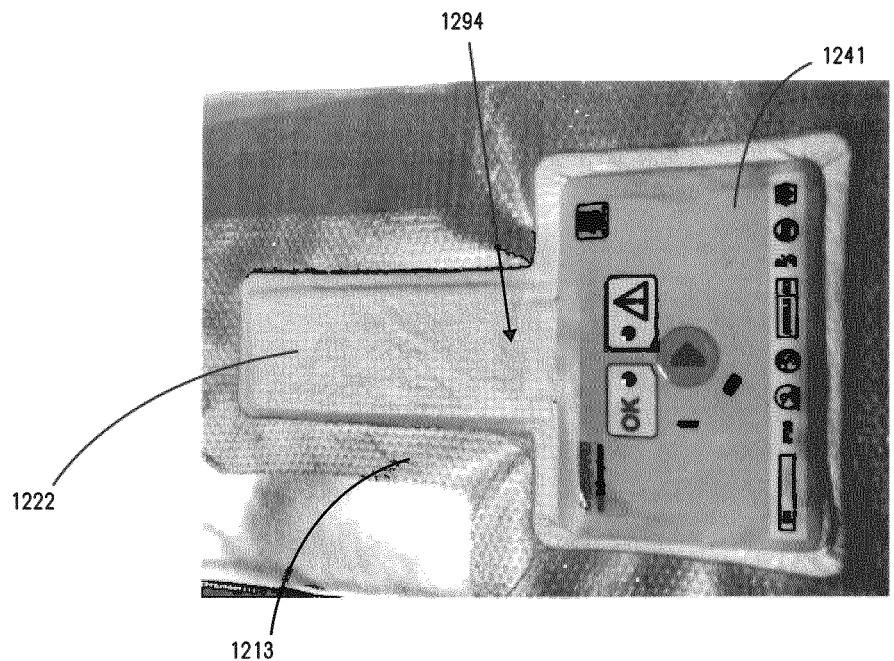
Figure 12D:
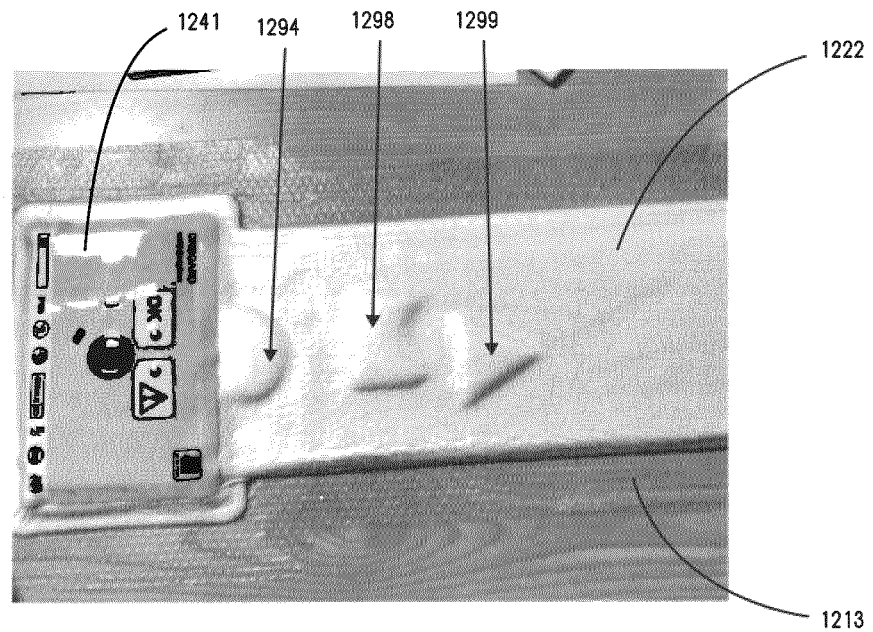
Figure 12E:
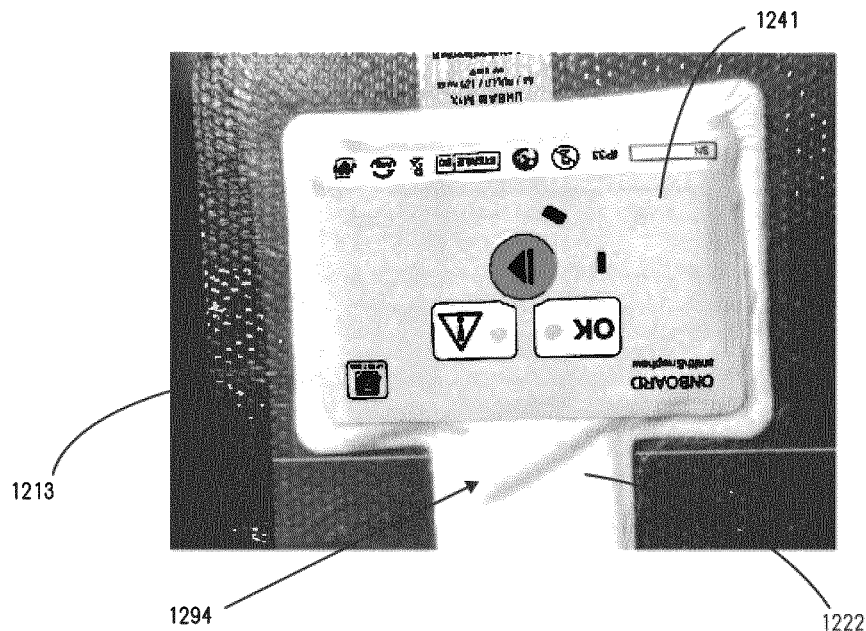
Figure 12F:
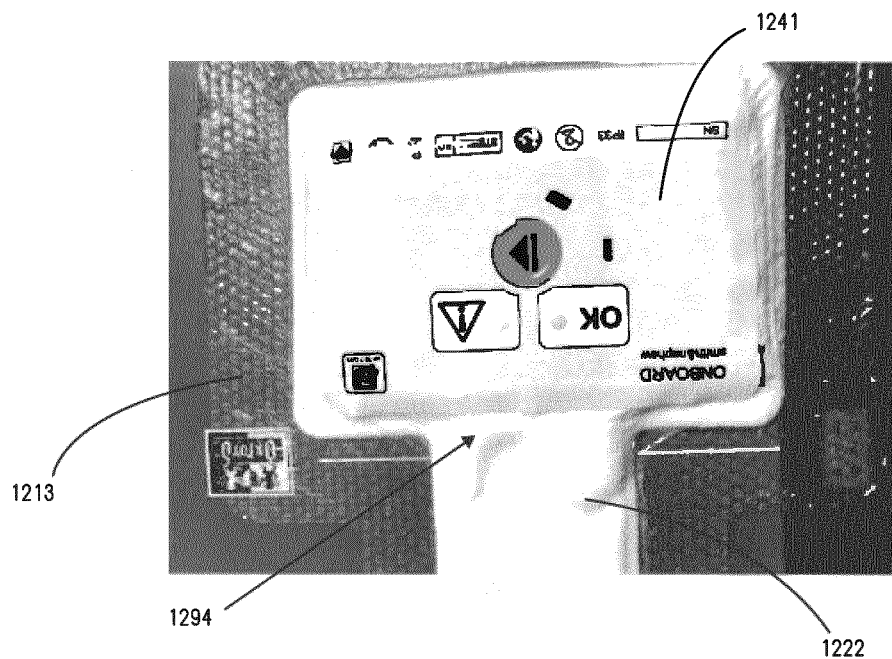
Figure 12G:
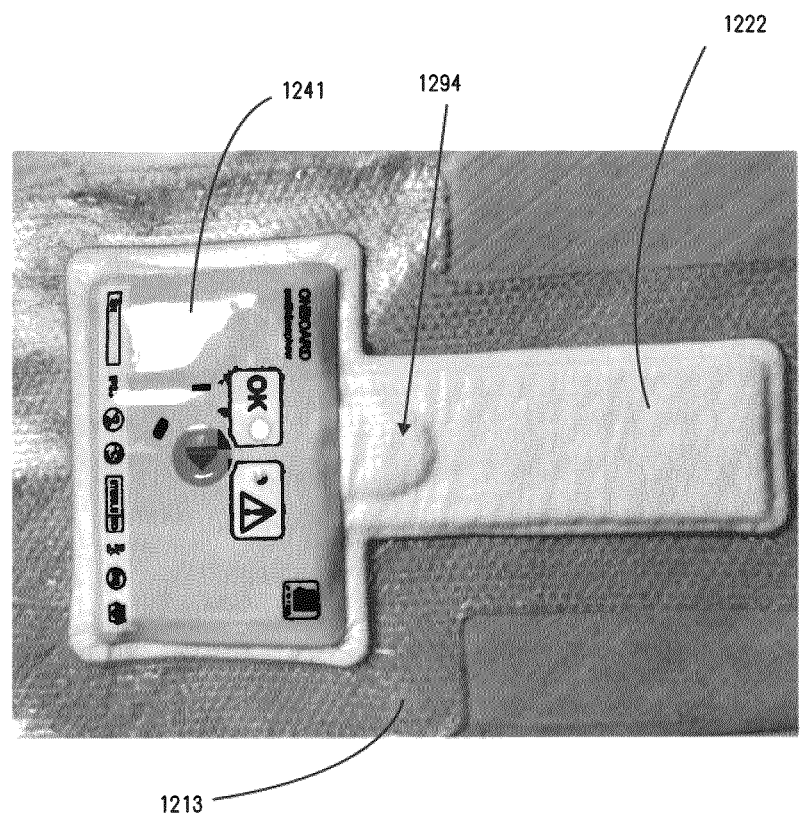

As illustrated in FIGS. 12A-12G a negative pressure indicator can be formed from an extension 1294 of any sizes and/or shapes of material. FIGS. 12A-12B illustrate embodiments of a triangle shaped extension 1294. FIG. 12C illustrates an embodiment of a rectangular shaped extension 1294. FIGS. 12D and 12G illustrate embodiments of an extension 1294 shaped as a semi-circle on a rectangle. FIG. 12D also illustrates an embodiment of other negative pressure indicators 1298 and 1299 that can be used in addition to or in place of the extension 1294. The negative pressure indicators 1298 and 1299 can be formed from indicator material layers. The negative pressure indicators 1298 and 1299 formed from indicator material layers can be individual or separate pieces of dressing material that can be applied to the laminated structure of the wound dressing. When negative pressure is applied to the wound dressing, the negative pressure indicators 1298 and 1299 can protrude from an upper surface of the wound dressing and can provide a visual or tactile indication of the application of negative pressure as illustrated in FIG. 12D. The negative pressure indicators 1298 and 1299 can be any shape and any size desired. For example, the indicators 1298 and 1299 can be a triangle, square, rectangle, circle, the shape of any letter or number, and/or any other shape desired. FIGS. 12E and 12F illustrate embodiments of extension 1294 in various shapes and cut-outs of the absorbent material.

In some embodiments, as illustrated in FIGS. 12A-12G, the electronics assembly with label 1241 can be formed so that label material is not positioned over the material of the extension 1294 and the extension 1294 can be visible through the transparent cover layer 1213. In other embodiments, the label 1241 can have an extended area so that the label 1241 covers the material of the extension 1294. This can allow for the user to easily recognize what portion of the dressing will contain the negative pressure indicator. The portion of the label 1241 that covers the extension 1294 can include indicia indicating that the protruding surface provides an indication of negative pressure.

In some embodiments, the large absorbent layer 1222 can be shaped to provide a visible indication when negative pressure has been applied or optimal negative pressure is reached.

Figure 13A:
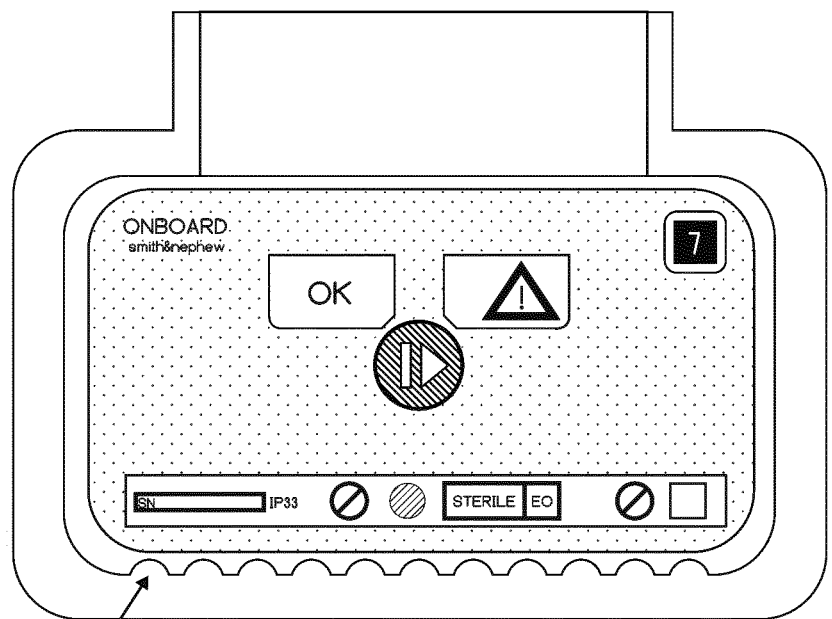

As illustrated in FIG. 13A, in some embodiments, the lower absorbent layer (i.e. the small absorbent layer 1115 shown in FIG. 11A-11B) can have small cut-outs 1397 in the absorbent material instead of the extension. The cut-outs 1397 can be used as negative pressure indicators similar to the negative pressure indicators described with reference to FIGS. 10A-10G, but, the cut-outs 1397 are formed in the lower absorbent layer. When negative pressure is applied and the dressing is compressed, the upper absorbent layer and the cover layer are compressed into the cut-outs and the cut-outs provide a visual and/or tactile indication of the application of negative pressure. The cut-outs 1397 can be a sawtooth pattern as illustrated in FIG. 13A. In some embodiments, the cut-outs 1397 can be any shape, size, or pattern to allow the material layers above the cut-outs to compress into the cut-outs.

Figure 13B:
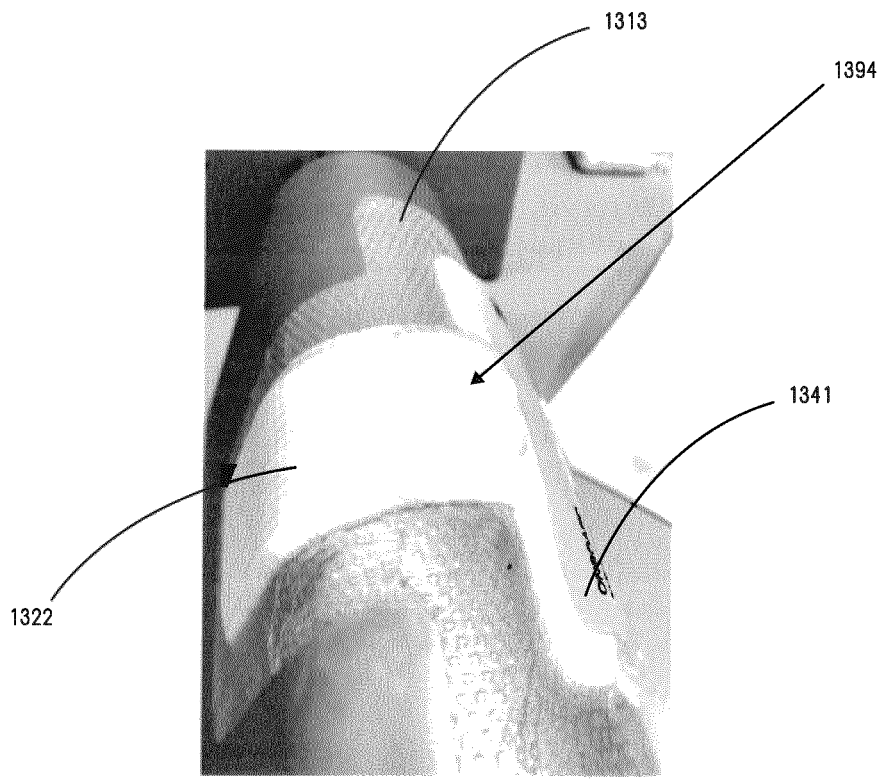

In some embodiments, the extension 1394 allows for a negative pressure indicator to be incorporated into the wound dressing while maintaining the flexibility and conformability of the dressing. FIG. 13B illustrates a wound dressing with a cover layer 1313, large absorbent layer 1322, label 1341, and a pressure indicator formed from an extension 1394. As illustrated in FIG. 13B, the extension 1394 can be visible when negative pressure is applied even when applied to a contoured or curved portion of a patient's body.

Figure 13C:
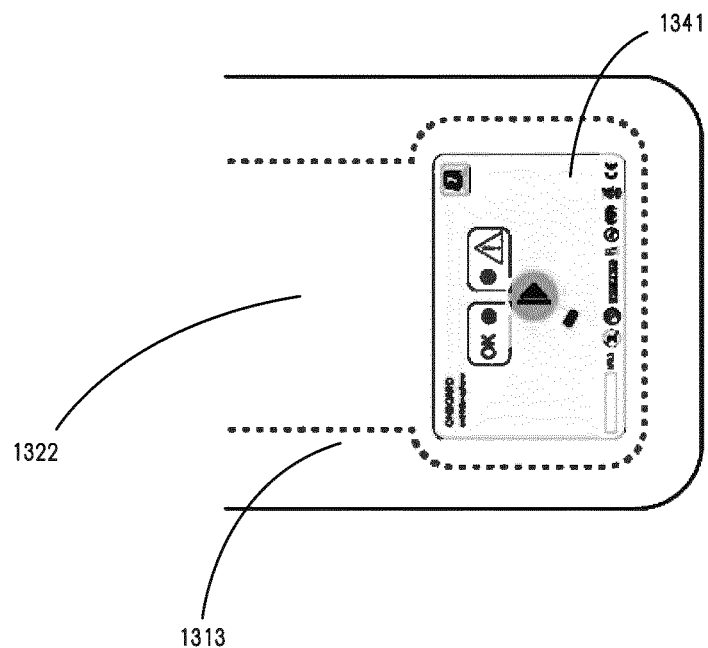
Figure 13D:
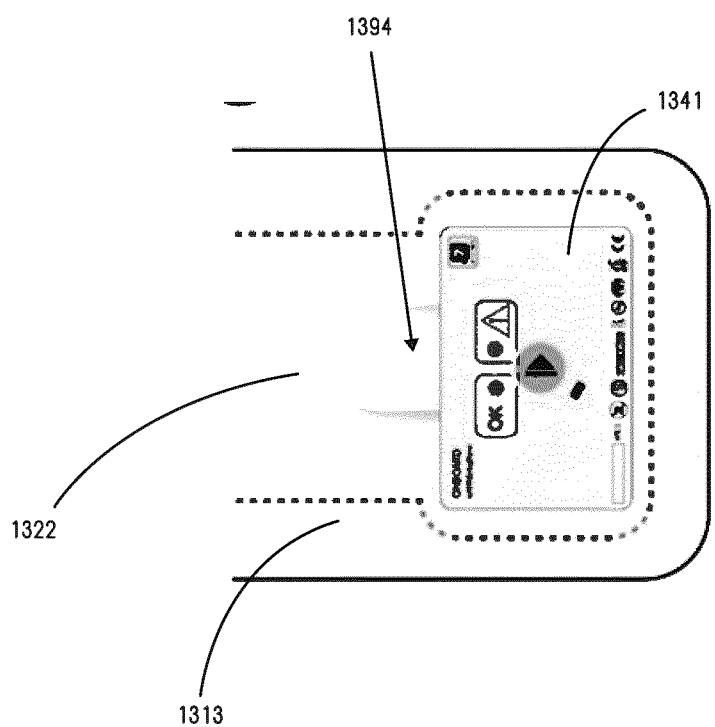

FIGS. 13C and 13D illustrate embodiments of a wound dressing with a cover layer 1313 and absorbent layer 1322, and label 1341. FIG. 13C illustrates an embodiment of the wound dressing prior to application of negative pressure. When the dressing is decompressed, the upper surface of the dressing will look and feel soft. The pressure indicator or extension is not visible from the upper surface of the device. FIG. 13D illustrates the wound dressing when negative pressure is applied. When the dressing is compressed, the extension 1394 is visible or detectable from the top surface of the device.

Figure 14A:
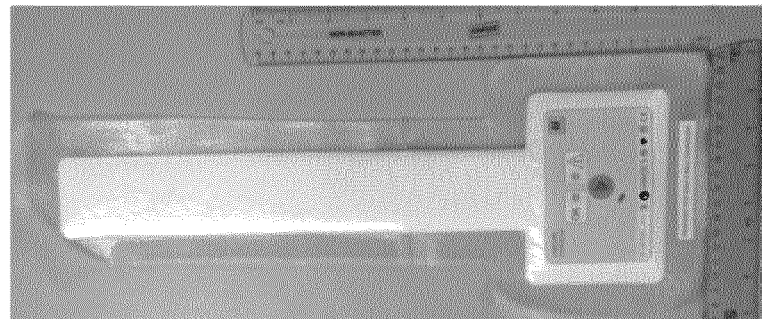
FIGS. 14A-14E illustrate embodiments of various shapes and sizes for the wound dressing incorporating an electronics assembly.
Figure 14B:
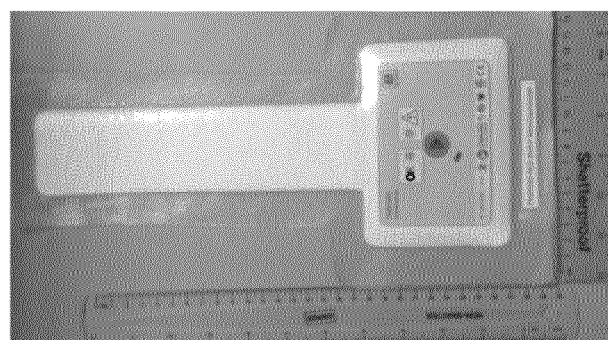
Figure 14C:
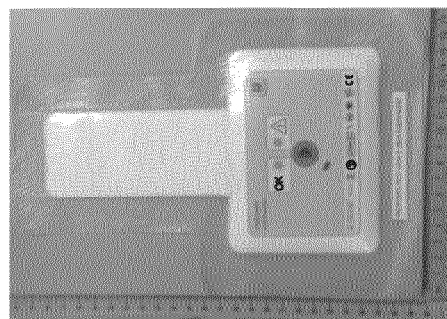
Figure 14D:
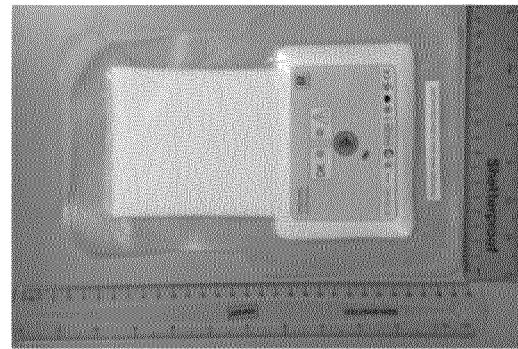
Figure 14E:
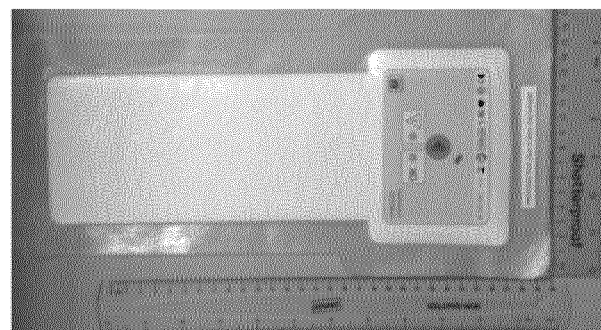

FIGS. 14A-14E illustrate embodiments of various shapes and sizes for the wound dressing incorporating an electronics assembly. The wound dressing with embedded electronics assembly can be any shape or size to accommodate various types of wounds and conform to the shapes and contours of the patient's body. For example, the wound dressing with embedded electronics can have a rectangular, rounded rectangular, square, T shaped, or any other shape or design. The wound dressing can have a longitudinal length that is parallel to a longitudinal axis that extends the length of the dressing passing through the electronics area and absorbent area. The absorbent area can have a longitudinal axis extending parallel to the longitudinal axis of the dressing. In some embodiments, the dressing has a length that is longer parallel to the longitudinal axis than it is wide. The electronics assembly can have a longitudinal axis that is perpendicular to the longitudinal axis of the absorbent area. In some embodiments, electronics assembly can have a length parallel to its longitudinal axis that is longer than it is wide. In some embodiments, the absorbent area of the wound dressing can be an elongated rectangular shape that includes a length of the absorbent area that is greater than the width of the absorbent area as illustrated in FIGS. 14A-14C, and 14E. In some embodiments, the absorbent area of the wound dressing can have a square shape that includes a length of the absorbent area that is substantially equal to or equal to the width of the absorbent area as illustrated in FIG. 14D. In some embodiments, the wound dressings with embedded electronics described herein can be rectangular or rounded rectangular shaped as illustrated with reference to FIGS. 1A-2B and 5A-5B. In other embodiments, the wound dressings with embedded electronics described herein can be T shaped as illustrated with reference to FIGS. 3A-3C and FIGS. 8-14E.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:
1. A wound dressing apparatus comprising:
    a wound dressing comprising:
        a first layer comprising a proximal wound-facing face, a distal face opposite the proximal wound-facing face, and one or more apertures;
        a cover layer configured to cover and form a seal over a wound and the first layer;
        an electronics assembly comprising a negative pressure source; and
        a non-adhesive film beneath the proximal wound-facing face of the first layer at least when negative pressure is applied;
    wherein a portion of the cover layer overlying the one or more apertures in the first layer is configured to be compressed within the one or more apertures in the first layer and contact the non-adhesive film when negative pressure is applied to the wound dressing apparatus;
    wherein the compressed cover layer indicates a level of negative pressure below the cover layer.

2. A wound dressing apparatus comprising:
a wound dressing comprising:
   a first layer comprising a proximal wound-facing face, a distal face opposite the proximal wound-facing face, and one or more apertures;
   a cover layer configured to cover and form a seal over a wound and the first layer; and
   a non-adhesive film positioned beneath the proximal wound-facing face of
the first layer when negative pressure is applied;
wherein a portion of the cover layer overlying the one or more apertures in the first layer is configured to be compressed within the one or more apertures in the first layer and contact the non-adhesive film when negative pressure is applied to the wound dressing apparatus;
wherein the compressed cover layer indicates a level of negative pressure below the cover layer.

3. The wound dressing apparatus of claim 2, further comprising a wound contact layer comprising a proximal wound-facing face and a distal face, the wound contact layer beneath the proximal wound-facing face of the first layer, wherein the proximal wound-facing face of the wound contact layer is configured to be positioned in contact with a wound.

4. The wound dressing apparatus of claim 3, wherein the non-adhesive film is configured to prevent the cover layer from remaining fixed in a compressed position within the one or more apertures.

5. The wound dressing apparatus of claim 2, further comprising an electronics assembly comprising a negative pressure source.

6. The wound dressing apparatus of claim 5, wherein the negative pressure source is positioned within the wound dressing.

7. The wound dressing apparatus of claim 5, wherein the one or more apertures are positioned in a portion of the first layer adjacent to the electronics assembly.

8. The wound dressing apparatus of claim 2, wherein the compressed cover layer is configured to provide a visual or a tactile indication of negative pressure.

9. The wound dressing apparatus of claim 2, wherein the compressed cover layer has a shape selected from a group consisting of a rectangle, a semi-circle on a rectangle, a triangle, and a semi-circle.

10. The wound dressing apparatus of claim 2, further comprising a transmission layer comprising a proximal wound-facing face and a distal face, the transmission layer positioned beneath the proximal wound-facing face of the first layer.

11. The wound dressing apparatus of claim 2, further comprising an electronics area and an absorbent area, wherein the absorbent area is configured to be positioned over the wound and the electronics area is configured to receive an electronics assembly positioned within the wound dressing.

12. The wound dressing apparatus of claim 11, further comprising a negative pressure source positioned within the wound dressing in the electronics area.

13. The wound dressing apparatus of claim 11, wherein the one or more apertures in the first layer are positioned at a portion of the absorbent area adjacent to the electronics area.

14. The wound dressing apparatus of claim 11, wherein the one or more apertures in the first layer are positioned within the absorbent area.

15. The wound dressing apparatus of claim 2, wherein the one or more apertures comprise circular shaped apertures between 3 mm to 7 mm in diameter.

16. The wound dressing apparatus of claim 2, wherein the one or more apertures in the first layer comprise an array of apertures.

17. The wound dressing apparatus of claim 16, wherein the array of apertures comprises three apertures in the array.

18. The wound dressing apparatus of claim 2, wherein the portion of the cover layer overlaying the one or more apertures in the first layer is further configured to be decompressed when the wound dressing apparatus is under ambient pressure.

19. The wound dressing apparatus of claim 2, wherein the first layer comprises an absorbent layer.

* * * * *